US011607349B2

United States Patent
Venturino

(10) Patent No.: US 11,607,349 B2
(45) Date of Patent: Mar. 21, 2023

(54) ABSORBENT CORES AND METHODS FOR FORMING ABSORBENT CORES

(71) Applicant: Kimberly-Clark Worldwide, Inc., Neenah, WI (US)

(72) Inventor: Michael B. Venturino, Appleton, WI (US)

(73) Assignee: KIMBERLY-CLARK WORLDWIDE, INC., Neenah, WI (US)

( * ) Notice: Subject to any disclaimer, the term of this patent is extended or adjusted under 35 U.S.C. 154(b) by 0 days.

(21) Appl. No.: 17/381,350

(22) Filed: Jul. 21, 2021

(65) Prior Publication Data

US 2021/0346209 A1    Nov. 11, 2021

Related U.S. Application Data

(63) Continuation of application No. 16/086,038, filed as application No. PCT/US2016/025190 on Mar. 31, 2016, now Pat. No. 11,135,097.

(51) Int. Cl.
*A61F 13/15*    (2006.01)
*A61F 13/535*    (2006.01)
*A61F 13/53*    (2006.01)

(52) U.S. Cl.
CPC .. *A61F 13/15634* (2013.01); *A61F 13/15764* (2013.01); *A61F 13/535* (2013.01);
(Continued)

(58) Field of Classification Search
CPC ........ A61F 2013/530802; A61F 2013/530481; A61F 2013/1591; A61F 2013/15406; A61F 13/535; A61F 13/15764; A61F 13/15634

See application file for complete search history.

(56) References Cited

U.S. PATENT DOCUMENTS

| 4,005,957 A | 2/1977 | Savich |
| 4,392,908 A | 7/1983 | Dehnel |

(Continued)

FOREIGN PATENT DOCUMENTS

| CN | 1122150 A | 5/1996 |
| CN | 1406566 A | 4/2003 |

(Continued)

OTHER PUBLICATIONS

Baer, Samuel C., Particle Containment And Immobilization In Roll Good Materials, INJ, Fall 2004, pp. 54-59.

(Continued)

*Primary Examiner* — Vishal I Patel
(74) *Attorney, Agent, or Firm* — Kimberly-Clark Worldwide, Inc.

(57) ABSTRACT

Pulpless absorbent cores and methods of manufacture are disclosed. A method of forming an absorbent core may comprise moving a forming surface in a machine direction, creating a pressure differential across the forming surface, advancing a base carrier sheet on the forming surface in the machine direction, applying a first adhesive onto the base carrier sheet, and applying a first quantity of particulate material onto the first adhesive at a first cross-machine direction width. The method may further comprise depositing a matrix of material onto the first quantity of particulate material at a second cross-machine direction width, the matrix of material comprising a second quantity of particulate material and a second adhesive, wherein the second cross-machine direction width is smaller than the first cross-machine direction width, and wherein the second quantity of particulate material and the adhesive are pre-mixed prior to deposition onto the first quantity of particulate material.

20 Claims, 20 Drawing Sheets

(52) U.S. Cl.
CPC ............... *A61F 2013/1591* (2013.01); *A61F 2013/15406* (2013.01); *A61F 2013/530481* (2013.01); *A61F 2013/530802* (2013.01)

(56) References Cited

U.S. PATENT DOCUMENTS

| | | | |
|---|---|---|---|
| 4,585,448 A | 4/1986 | Enloe | |
| 4,666,647 A | 5/1987 | Enloe et al. | |
| 4,679,704 A | 7/1987 | Dunlop et al. | |
| 4,685,915 A | 8/1987 | Hasse et al. | |
| 4,764,325 A | 8/1988 | Angstadt | |
| 5,017,324 A | 5/1991 | Kaiser et al. | |
| 5,028,224 A | 7/1991 | Pieper et al. | |
| 5,028,225 A | 7/1991 | Staheli | |
| 5,156,902 A | 10/1992 | Pieper et al. | |
| 5,213,817 A | 5/1993 | Pelley | |
| 5,279,854 A | 1/1994 | Kendall et al. | |
| 5,415,716 A | 5/1995 | Kendall | |
| 5,429,788 A | 7/1995 | Ribble et al. | |
| 5,447,677 A | 9/1995 | Griffoul et al. | |
| 5,494,622 A | 2/1996 | Heath et al. | |
| 5,514,324 A | 5/1996 | Bachar | |
| 5,516,569 A | 5/1996 | Veith et al. | |
| 5,750,066 A | 5/1998 | Vonderhaar et al. | |
| 5,763,331 A | 6/1998 | Demhartner | |
| 5,766,388 A | 6/1998 | Pelley et al. | |
| 5,983,457 A | 11/1999 | Toney et al. | |
| 6,080,909 A | 6/2000 | Osterdahl et al. | |
| 6,093,474 A | 7/2000 | Sironi | |
| 6,162,959 A | 12/2000 | Lawrence | |
| 6,330,735 B1 | 12/2001 | Hahn et al. | |
| 6,403,857 B1 | 6/2002 | Gross et al. | |
| 6,459,016 B1 | 10/2002 | Rosenfeld et al. | |
| 6,664,439 B1 | 12/2003 | Arndt et al. | |
| 6,703,846 B2 | 3/2004 | Delzer et al. | |
| 6,706,129 B2 | 3/2004 | Ando et al. | |
| 6,932,929 B2 | 8/2005 | Krautkramer et al. | |
| 6,972,011 B2 | 12/2005 | Maeda et al. | |
| 7,121,818 B2 | 10/2006 | Driskell | |
| 7,527,823 B2 | 5/2009 | Tombült-Meyer et al. | |
| 7,717,150 B2 | 5/2010 | Manabe et al. | |
| 7,872,168 B2 | 1/2011 | Sawyer et al. | |
| 7,906,065 B1 | 3/2011 | Brown et al. | |
| 7,938,813 B2 | 5/2011 | Wang et al. | |
| 8,148,598 B2 | 4/2012 | Tsang et al. | |
| 8,324,446 B2 | 12/2012 | Wang et al. | |
| 8,485,347 B2 | 7/2013 | Jackels | |
| 8,552,251 B2 | 10/2013 | Zhou et al. | |
| 8,852,381 B2 | 10/2014 | Nhan et al. | |
| 8,855,979 B2 | 10/2014 | Blessing et al. | |
| 8,960,122 B2 | 2/2015 | Yano et al. | |
| 9,033,018 B2 | 5/2015 | Ogasawara et al. | |
| 9,044,359 B2 | 6/2015 | Wciorka et al. | |
| 10,918,529 B2 | 2/2021 | Venturino et al. | |
| 2002/0169430 A1 | 11/2002 | Kirk et al. | |
| 2003/0044562 A1 | 3/2003 | Li et al. | |
| 2003/0111774 A1 | 6/2003 | Kellenberger et al. | |
| 2003/0129915 A1 | 7/2003 | Harriz | |
| 2003/0130638 A1 | 7/2003 | Baker | |
| 2003/0134559 A1 | 7/2003 | Delzer et al. | |
| 2003/0212376 A1 | 11/2003 | Walter et al. | |
| 2003/0236510 A1 | 12/2003 | Yasumura et al. | |
| 2005/0148972 A1 | 7/2005 | Miyama et al. | |
| 2006/0141891 A1 | 6/2006 | Melius et al. | |
| 2008/0132863 A1 | 6/2008 | Waksmundzki et al. | |
| 2009/0018517 A1 | 1/2009 | Cecconi et al. | |
| 2009/0198205 A1 | 8/2009 | Malowaniec et al. | |
| 2010/0051166 A1 | 3/2010 | Hundorf et al. | |
| 2010/0228209 A1 | 9/2010 | Carlucci et al. | |
| 2010/0312208 A1 | 12/2010 | Bond et al. | |
| 2011/0041999 A1 | 2/2011 | Hundorf et al. | |
| 2011/0152809 A1 | 6/2011 | Carlucci et al. | |
| 2012/0024470 A1 | 2/2012 | Hundorf et al. | |
| 2012/0316523 A1 | 12/2012 | Hippe et al. | |
| 2012/0316524 A1 | 12/2012 | Thomann et al. | |
| 2012/0316528 A1 | 12/2012 | Kreuzer et al. | |
| 2013/0112348 A1 | 5/2013 | Blessing et al. | |
| 2013/0165882 A1 | 6/2013 | Kawakami et al. | |
| 2013/0226119 A1 | 8/2013 | Katsuragawa et al. | |
| 2013/0240139 A1 | 9/2013 | Zhou et al. | |
| 2013/0331806 A1 | 12/2013 | Rosati et al. | |
| 2014/0005623 A1 | 1/2014 | Wirtz et al. | |
| 2014/0005625 A1 | 1/2014 | Wirtz et al. | |
| 2014/0027943 A1 | 1/2014 | Hoshika | |
| 2014/0163503 A1 | 6/2014 | Arizti et al. | |
| 2014/0163504 A1 | 6/2014 | Bianchi et al. | |
| 2014/0261987 A1 | 9/2014 | Chartrel | |
| 2014/0276509 A1 | 9/2014 | Ducker et al. | |
| 2014/0303582 A1 | 10/2014 | Wright et al. | |
| 2014/0308483 A1 | 10/2014 | Li | |
| 2014/0324008 A1* | 10/2014 | Hundorf .......... A61F 13/5323 604/366 |
| 2014/0329672 A1 | 11/2014 | Colclough, Jr. et al. | |
| 2015/0005727 A1 | 1/2015 | Matsushita et al. | |
| 2015/0011960 A1 | 1/2015 | Arayama et al. | |
| 2015/0065974 A1 | 3/2015 | Michiels et al. | |
| 2015/0080821 A1 | 3/2015 | Peri et al. | |
| 2015/0094682 A1 | 4/2015 | Fell et al. | |
| 2015/0245952 A1 | 9/2015 | Gahan | |
| 2015/0245958 A1 | 9/2015 | Chmielewski et al. | |
| 2015/0359683 A1 | 12/2015 | Jackels et al. | |
| 2017/0095380 A1 | 4/2017 | Wirtz et al. | |
| 2017/0258955 A1 | 9/2017 | Lindner et al. | |
| 2017/0312146 A1 | 11/2017 | Bianchi et al. | |
| 2019/0159946 A1 | 5/2019 | Descheemaecker et al. | |
| 2020/0289355 A1 | 9/2020 | Robran | |
| 2021/0085530 A1 | 3/2021 | Venturino et al. | |

FOREIGN PATENT DOCUMENTS

| | | |
|---|---|---|
| CN | 1736355 A | 2/2006 |
| CN | 1853013 A | 10/2006 |
| CN | 101070458 A | 11/2007 |
| CN | 101978107 A | 2/2011 |
| CN | 102065816 A | 5/2011 |
| CN | 102281852 A | 12/2011 |
| CN | 102686395 A | 9/2012 |
| CN | 102844009 A | 12/2012 |
| CN | 102883695 A | 1/2013 |
| CN | 103179931 A | 6/2013 |
| CN | 103202746 A | 7/2013 |
| CN | 104066407 A | 9/2014 |
| CN | 104394823 A | 3/2015 |
| CN | 104507438 A | 4/2015 |
| CN | 108779594 A | 11/2018 |
| EP | 0611607 A1 | 8/1994 |
| EP | 0463716 B1 | 6/1999 |
| EP | 1110528 A2 | 6/2001 |
| EP | 0700673 B1 | 3/2002 |
| EP | 1253231 B1 | 11/2005 |
| EP | 1697057 B1 | 11/2007 |
| EP | 2532330 A1 | 12/2012 |
| EP | 2679210 B1 | 1/2015 |
| JP | H07213552 A | 8/1995 |
| JP | 11320742 A | 11/1999 |
| JP | 2001145659 A | 5/2001 |
| JP | 2015181785 A | 10/2015 |
| WO | 2007122525 A1 | 11/2007 |
| WO | 2014145312 A2 | 9/2014 |

OTHER PUBLICATIONS

Industry News—Live from Index 2014, Ultrasonic diaper core former Helixbond, http://shows.nonwovens-industry.com/index2014/news/40624.

* cited by examiner

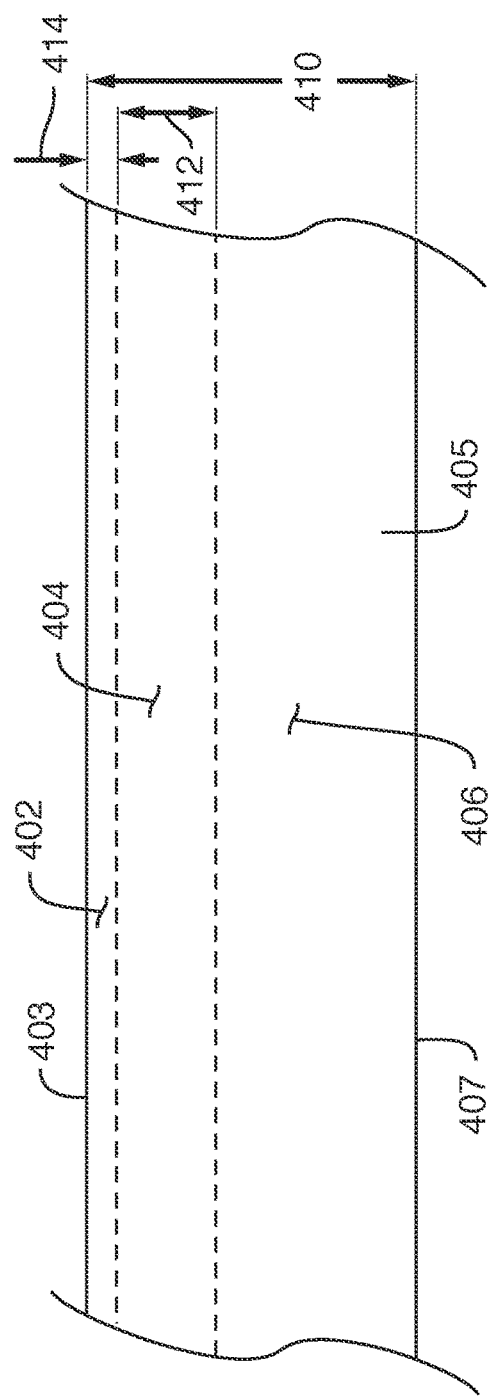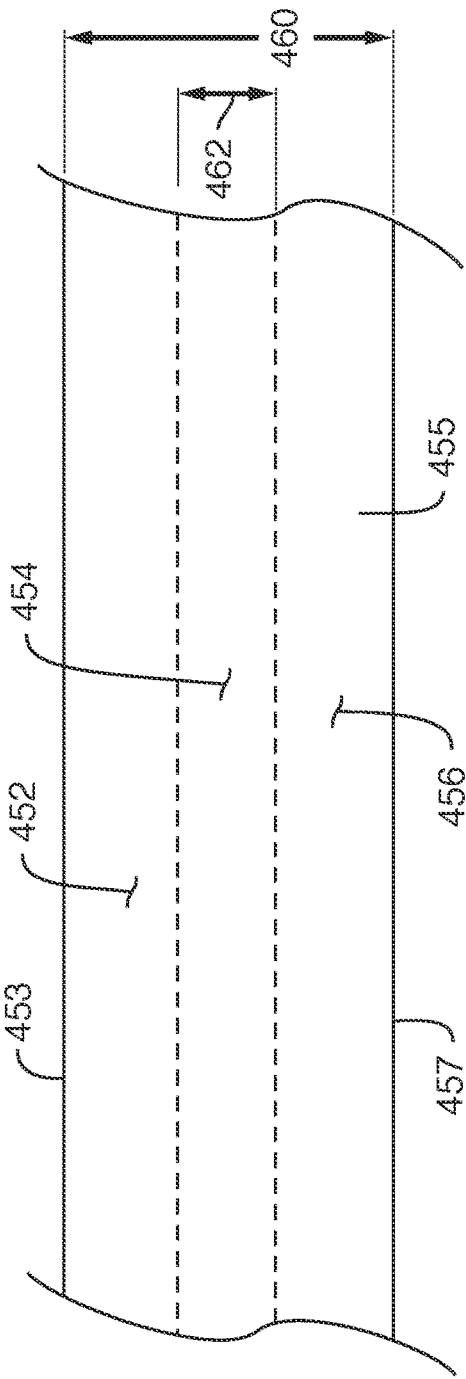

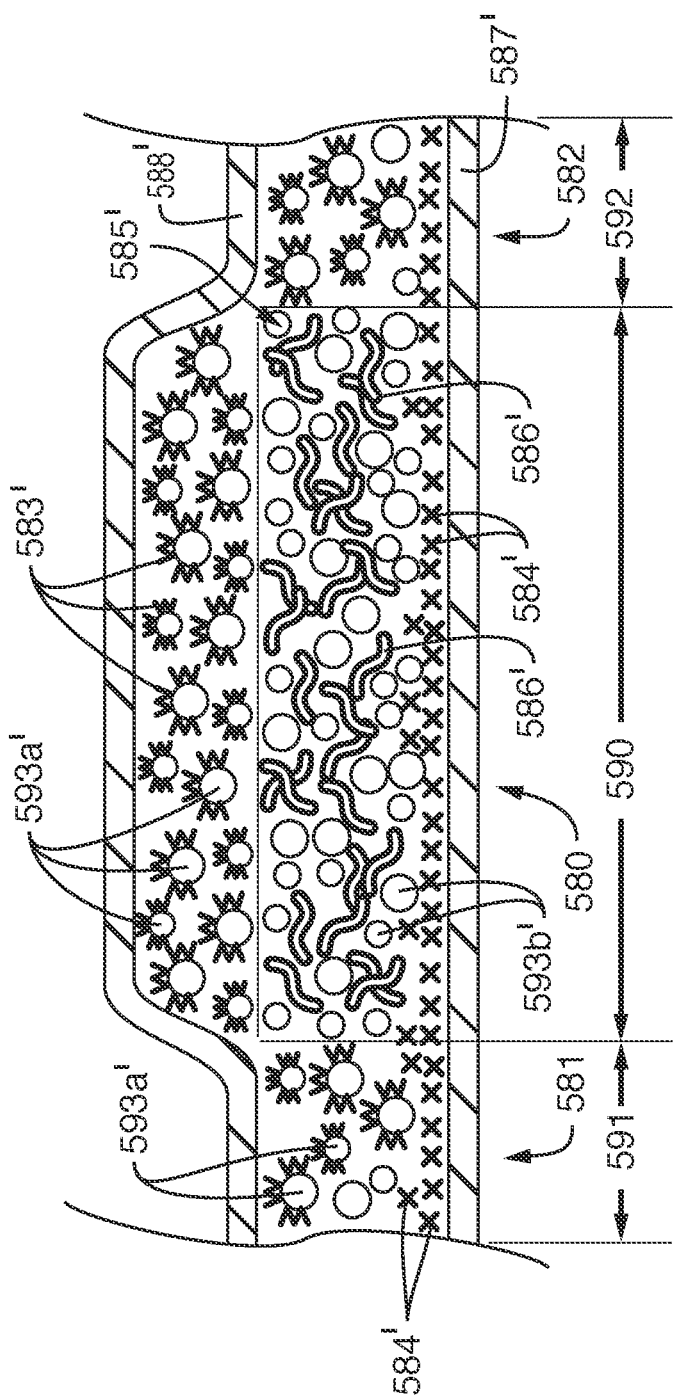

ABSORBENT CORES AND METHODS FOR FORMING ABSORBENT CORES

The present application is a continuation application and claims priority to U.S. patent application Ser. No. 16/086,038, filed on Sep. 18, 2018, which is a national-phase entry, under 35 U.S.C. § 371, of PCT Patent Application No. PCT/US16/25190, filed on Mar. 31, 2016, all of which are incorporated herein by reference.

FIELD OF THE INVENTION

The field of this disclosure relates generally to absorbent cores and methods of manufacturing absorbent cores for use in absorbent articles, and more specifically to pulpless absorbent cores and methods of forming pulpless absorbent cores for use in absorbent articles, such as diapers, training pants, incontinence products, disposable underwear, medical garments, feminine care articles, absorbent swim wear, and the like.

BACKGROUND

Absorbent cores are used in different types of products to control and contain bodily fluids and other bodily liquid discharge. Many present absorbent cores include pulp fluff, which acts to absorb the discharged liquids. Present absorbent articles can also contain particulate absorbent material, such as superabsorbent material, mixed in with the pulp fluff. The particulate absorbent material has a higher absorbent capacity than the pulp fluff, and the inclusion of particulate absorbent material can greatly increase the absorbent capacity of the absorbent cores. In these instances, the pulp fluff works not only to help absorb discharged fluids, but also to stabilize the particulate absorbent material, for instance maintaining the location of the particulate absorbent material within the absorbent cores. However, the pulp fluff in these absorbent cores imparts a significant amount of bulk to the absorbent cores. Accordingly, absorbent cores that have a high absorbent capacity yet do not contain pulp fluff, or do not contain a substantial amount of pulp fluff, in order to reduce bulk may be desirable.

BRIEF SUMMARY OF THE INVENTION

This disclosure relates generally to absorbent cores and methods of manufacturing absorbent cores for use in absorbent articles, and more specifically to pulpless absorbent cores and methods of forming pulpless absorbent cores for use in absorbent articles, such as diapers, training pants, incontinence products, disposable underwear, medical garments, feminine care articles, absorbent swim wear, and the like.

In a first embodiment, a method for forming an absorbent core may comprise moving a forming member in a machine direction, the forming member having a foraminous forming surface, creating a pressure differential across the foraminous forming surface, advancing a base carrier sheet on the foraminous forming surface in the machine direction, applying a first adhesive onto the base carrier sheet, and applying a first quantity of particulate material onto the first adhesive at a first cross-machine direction width. In some embodiments, the method may further comprise depositing a matrix of material onto the first quantity of particulate material at a second cross-machine direction width, the matrix of material comprising a second quantity of particulate material and a second adhesive, wherein the second cross-machine direction width is smaller than the first cross-machine direction width, and wherein the second quantity of particulate material and the adhesive are pre-mixed prior to deposition onto the first quantity of particulate material.

Additionally, or alternatively, in further embodiments according to the first embodiment, the method may further comprise applying a third adhesive onto the first quantity of particulate material before depositing the matrix of material onto the first quantity of particulate material.

Additionally, or alternatively, in further embodiments according to the above embodiment, the third adhesive may comprise a spray application aqueous binder (SAAB) adhesive.

Additionally, or alternatively, in further embodiments according to any of the above embodiments with respect to the first embodiment, the method may further comprise applying a top carrier sheet onto the matrix of material.

Additionally, or alternatively, in further embodiments according to any of the above embodiments with respect to the first embodiment, the method may further comprise folding the base carrier sheet to form a top carrier sheet.

Additionally, or alternatively, in further embodiments according to any of the above embodiments with respect to the first embodiment, a third adhesive may be applied onto the matrix of material.

Additionally, or alternatively, in further embodiments according to the above embodiment, the method may further comprise applying a top carrier sheet onto the third adhesive.

Additionally, or alternatively, in further embodiments according to any of the above embodiments with respect to the first embodiment, the second cross-machine direction width may have a value that is between one-quarter and three-quarters of a value of the first cross-machine direction width.

Additionally, or alternatively, in further embodiments according to any of the above embodiments with respect to the first embodiment, the base carrier sheet may comprise a left edge region, a center region, and a right edge region, and the matrix of material may be deposited throughout the center region such that the center region has a higher basis weight than either of the first edge region and the second edge region.

Additionally, or alternatively, in further embodiments according to any of the above embodiments with respect to the first embodiment, the basis weight of the center region may comprise between 150% and 400% of the basis weight of either of the first edge region or the second edge region.

Additionally, or alternatively, in further embodiments according to any of the above embodiments with respect to the first embodiment, at least 33% of a total amount of particulate material of the absorbent core may be disposed within the center region Additionally, or alternatively, in further embodiments according to any of the above embodiments with respect to the first embodiment, the method may further comprise applying cellulose fibers onto the base carrier sheet.

Additionally, or alternatively, in further embodiments according to the above embodiment, the cellulose fibers and the first quantity of particulate material are mixed together.

Additionally, or alternatively, in further embodiments according to any of the above embodiments with respect to the first embodiment, the first quantity of particulate material may comprise super absorbent material (SAM).

Additionally, or alternatively, in further embodiments according to any of the above embodiments with respect to the first embodiment, the second quantity of particulate material may comprise super absorbent material (SAM).

Additionally, or alternatively, in further embodiments according to any of the above embodiments with respect to the first embodiment, the second quantity of particulate material may comprise at least 25%, by weight, of a total particulate material content of the absorbent core.

Additionally, or alternatively, in further embodiments according to any of the above embodiments with respect to the first embodiment, the second quantity of particulate material may comprise at least 50%, by weight, of a total particulate material content of the absorbent core.

Additionally, or alternatively, in further embodiments according to any of the above embodiments with respect to the first embodiment, the second quantity of particulate material may comprise at least 75%, by weight, of a total particulate material content of the absorbent core.

In a second embodiment, a method of forming an absorbent core may comprise advancing a base carrier sheet on a foraminous forming member in a machine direction, creating a pressure differential across the foraminous forming member, and depositing a matrix of material onto the base carrier sheet at a first cross-machine direction width, the matrix of material comprising a first quantity of particulate material and a first adhesive. In some additional embodiments, the method may further comprise applying a second quantity of particulate material onto the base carrier sheet and the matrix of material at a second cross-machine direction width, wherein the first cross-machine direction width is smaller than the second cross-machine direction width, and wherein the first quantity of particulate material and the adhesive are pre-mixed prior to deposition onto the base carrier sheet.

Additionally, or alternatively, in further embodiments according to the second embodiment, the method may further comprise applying a top carrier sheet onto the second quantity of particulate material.

Additionally, or alternatively, in further embodiments according to any of the above embodiments with respect to the second embodiment, the first cross-machine direction width may have a value that is between one-quarter and three-quarters of a value of the second cross-machine direction width.

Additionally, or alternatively, in further embodiments according to any of the above embodiments with respect to the second embodiment, the first cross-machine direction width may have a value that is between one-third and two-thirds of a value of the second cross-machine direction width Additionally, or alternatively, in further embodiments according to any of the above embodiments with respect to the second embodiment, the method may further comprise injecting air toward streams of particulate material and adhesive to mix the streams of the particulate material and the adhesive prior to the particulate material and the adhesive being deposited as a matrix of material at the forming surface.

Additionally, or alternatively, in further embodiments according to any of the above embodiments with respect to the second embodiment, the first quantity of particulate material may further comprise cellulose fibers.

Additionally, or alternatively, in further embodiments according to any of the above embodiments with respect to the second embodiment, the first quantity of particulate material may comprise super absorbent material (SAM).

Additionally, or alternatively, in further embodiments according to any of the above embodiments with respect to the second embodiment, the second quantity of particulate material may comprise SAM.

Additionally, or alternatively, in further embodiments according to any of the above embodiments with respect to the second embodiment, the second quantity of particulate material may comprise a mixture of cellulose fibers and particulate material.

Additionally, or alternatively, in further embodiments according to any of the above embodiments with respect to the second embodiment, the method may further comprise applying a second adhesive onto the base carrier sheet.

Additionally, or alternatively, in further embodiments according to any of the above embodiments with respect to the second embodiment, the method may further comprise applying a second adhesive onto the first quantity of particulate material.

Additionally, or alternatively, in further embodiments according to any of the above embodiments with respect to the second embodiment, the method may further comprise applying a third adhesive onto the top carrier sheet.

Additionally, or alternatively, in further embodiments according to any of the above embodiments with respect to the second embodiment, the particulate material within the matrix of material may comprise at least 25%, by weight, of a total particulate material content of the absorbent core.

Additionally, or alternatively, in further embodiments according to any of the above embodiments with respect to the second embodiment, the base carrier sheet may comprise a left edge region, a center region, and a right edge region, and the center region may have a higher basis weight than either of the first edge region and the second edge region after applying the second quantity of particulate material.

Additionally, or alternatively, in further embodiments according to any of the above embodiments with respect to the second embodiment, the basis weight of the center region may comprise between 150% and 400% of the basis weight of either of the first edge region or the second edge region after applying the second quantity of particulate material.

Additionally, or alternatively, in further embodiments according to any of the above embodiments with respect to the second embodiment, the method may further comprise applying a second adhesive onto the second quantity of particulate material.

Additionally, or alternatively, in further embodiments according to any of the above embodiments with respect to the second embodiment, the second adhesive may comprise a spray application aqueous binder (SAAB) adhesive.

In a third embodiment, an apparatus for forming absorbent cores may comprise a forming member having a forming surface that is moveable in a machine direction, the forming surface having a forming surface width extending in a cross-machine direction, a first adhesive applicator, a particulate material delivery chamber, the first particulate material delivery chamber comprising a first particulate material inlet configured for dispensing a first quantity of particulate material towards the forming surface, and a matrix delivery assembly, the matrix delivery assembly comprising a second particulate material inlet and one or more adhesive applicator nozzles configured for dispensing a second quantity of particulate material and adhesive toward the forming surface in a manner such that the second quantity of particulate material and adhesive comingle before depositing at the forming surface.

Additionally, or alternatively, in further embodiments according to the third embodiment, the particulate material delivery chamber may be configured for dispensing the first quantity of particulate material towards the forming surface such that the first quantity of particulate material is deposited at the forming surface at a first cross-machine direction width, the matrix delivery assembly may be configured for dispensing the second quantity of particulate material and adhesive toward the forming surface such that the second quantity of particulate material and adhesive are deposited at the forming surface at a second cross-machine direction width, and the second cross-machine direction width may be less than the first cross-machine direction width.

Additionally, or alternatively, in further embodiments according to the above embodiment, the second cross-machine direction width may have a value that is between one-quarter and three-quarters of a value of the first cross-machine direction width.

Additionally, or alternatively, in further embodiments according to any of the above embodiments with respect the third embodiment, the first particulate material delivery chamber may be disposed prior to the matrix delivery assembly in the machine direction.

Additionally, or alternatively, in further embodiments according to any of the above embodiments with respect the third embodiment, the matrix delivery assembly may be disposed prior to the particulate material delivery chamber in the machine direction.

Additionally, or alternatively, in further embodiments according to any of the above embodiments with respect the third embodiment, the apparatus may further comprise a third adhesive applicator disposed after the first adhesive applicator in the machine direction.

Additionally, or alternatively, in further embodiments according to the above embodiment, the first adhesive applicator may be configured to dispense hot-melt adhesive, and the third adhesive applicator may be configured to dispense a spray-application aqueous binder (SAAB) adhesive.

In a fourth embodiment, an absorbent core may comprise a base carrier sheet, a first adhesive disposed directly onto at least a portion of the base carrier sheet, a first quantity of particulate material disposed on the first adhesive, a matrix of material comprising a second quantity of particulate material and adhesive disposed on the first quantity of particulate material, and a top carrier sheet disposed on the matrix of material.

Additionally, or alternatively, in further embodiments according to the fourth embodiment, the absorbent core may further comprise a second adhesive disposed on the first quantity of particulate material.

Additionally, or alternatively, in further embodiments according to the above embodiment, the absorbent core may further comprise a third adhesive disposed on the matrix of material.

Additionally, or alternatively, in further embodiments according to the fourth embodiments according to any of the above embodiments with respect to the fourth embodiment, the absorbent core may further comprise a second adhesive disposed on the matrix of material.

Additionally, or alternatively, in further embodiments according to any of the above embodiments with respect to the fourth embodiment, the first quantity of particulate material may further comprise cellulose fibers.

Additionally, or alternatively, in further embodiments according to any of the above embodiments with respect to the fourth embodiment, the first quantity of particulate material may comprise superabsorbent material (SAM).

Additionally, or alternatively, in further embodiments according to any of the above embodiments with respect to the fourth embodiment, the second quantity of particulate material may comprise SAM.

Additionally, or alternatively, in further embodiments according to any of the above embodiments with respect to the fourth embodiment, the base carrier sheet and the top carrier sheet may comprise a single carrier sheet.

Additionally, or alternatively, in further embodiments according to any of the above embodiments with respect to the fourth embodiment, the absorbent core may have a machine direction length and a cross-machine direction width, and wherein a cross-machine direction width of the matrix of material may be less than a cross-machine direction width of the first quantity of particulate material.

Additionally, or alternatively, in further embodiments according to any of the above embodiments with respect to the fourth embodiment, the second quantity of particulate material may comprise at least 25%, by weight, of a total particulate material content of the absorbent core.

Additionally, or alternatively, in further embodiments according to any of the above embodiments with respect to the fourth embodiment, the second quantity of particulate material may comprise at least 50%, by weight, of a total particulate material content of the absorbent core.

Additionally, or alternatively, in further embodiments according to any of the above embodiments with respect to the fourth embodiment, the second quantity of particulate material in the matrix layer may comprise at least 75%, by weight, of a total particulate material content of the absorbent core.

In a fifth embodiment, an absorbent core may comprise one or more outer sheets forming an enclosure, the one or more outer sheets having an externally oriented face and an internally oriented face, a first quantity of particulate material disposed within the enclosure, and a matrix of material comprising a second quantity of particulate material and adhesive disposed adjacent the first quantity of particulate material within the enclosure.

Additionally, or alternatively, in further embodiments according the fifth embodiment, the absorbent core may further comprise an adhesive disposed between the first quantity of particulate material and the internally oriented face of the enclosure.

Additionally, or alternatively, in further embodiments according to any of the above embodiments with respect to the fifth embodiment, the absorbent core may further comprise an adhesive disposed between the matrix of material and the internally oriented face of the enclosure.

Additionally, or alternatively, in further embodiments according to any of the above embodiments with respect to the fifth embodiment, the second quantity of particulate material may comprise at least 25%, by weight, of a total particulate material content of the absorbent core.

Additionally, or alternatively, in further embodiments according to any of the above embodiments with respect to the fourth embodiment, the second quantity of particulate material may comprise at least 50%, by weight, of a total particulate material content of the absorbent core.

Additionally, or alternatively, in further embodiments according to any of the above embodiments with respect to the fourth embodiment, the second quantity of particulate material may comprise at least 75%, by weight, of a total particulate material content of the absorbent core.

In a sixth embodiment, an absorbent core may comprise a base carrier sheet having a carrier sheet cross-machine direction width, a first adhesive disposed directly on the base carrier sheet, a first quantity of particulate material disposed on the first adhesive, the first quantity of particulate material having a first particulate cross-machine direction width, a matrix of material comprising a second quantity of particulate material and adhesive disposed on the first quantity of particulate material, the matrix of material having a matrix cross-machine direction width, and a top carrier sheet disposed on the matrix of material. In some further embodiments, the matrix of material cross-machine direction width may be less than the first particulate cross-machine direction width.

Additionally, or alternatively, in further embodiments according the sixth embodiment, the absorbent core may further comprise a second adhesive disposed directly on the first quantity of particulate material between the first quantity of particulate material and the matrix layer of material.

Additionally, or alternatively, in further embodiments according to any of the above embodiments with respect to the sixth embodiment, the absorbent core may further comprise a second adhesive disposed on the matrix of material between the matrix of material and the top carrier sheet.

Additionally, or alternatively, in further embodiments according to any of the above embodiments with respect to the sixth embodiment, the first adhesive and the second adhesive may comprise different adhesives.

Additionally, or alternatively, in further embodiments according to any of the above embodiments with respect to the sixth embodiment, the first adhesive may comprise a holt-melt adhesive.

Additionally, or alternatively, in further embodiments according to any of the above embodiments with respect to the sixth embodiment, the second adhesive may comprise hot-melt adhesive.

Additionally, or alternatively, in further embodiments according to any of the above embodiments with respect to the sixth embodiment, the second adhesive may comprise a spray application aqueous-binder (SAAB) adhesive.

Additionally, or alternatively, in further embodiments according to any of the above embodiments with respect to the fifth embodiment, the first quantity of particulate material may further comprise cellulose fibers.

Additionally, or alternatively, in further embodiments according to any of the above embodiments with respect to the sixth embodiment, the first quantity of particulate material may comprise superabsorbent material (SAM).

Additionally, or alternatively, in further embodiments according to any of the above embodiments with respect to the sixth embodiment, the second quantity of particulate material may comprise SAM.

BRIEF DESCRIPTION OF THE DRAWINGS

FIGS. 14A and 14B are illustrations of carrier sheets that may be used to form absorbent cores.

FIG. 19 depicts a cross-section of another exemplary absorbent core taken along line B-B' in FIG. 17 which includes a matrix layer.

DETAILED DESCRIPTION OF THE DRAWINGS

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements. Moreover, the use of "top", "bottom", "above", "below" and variations of these terms is made for convenience, and does not require any particular orientation of the components.

Figure 1:
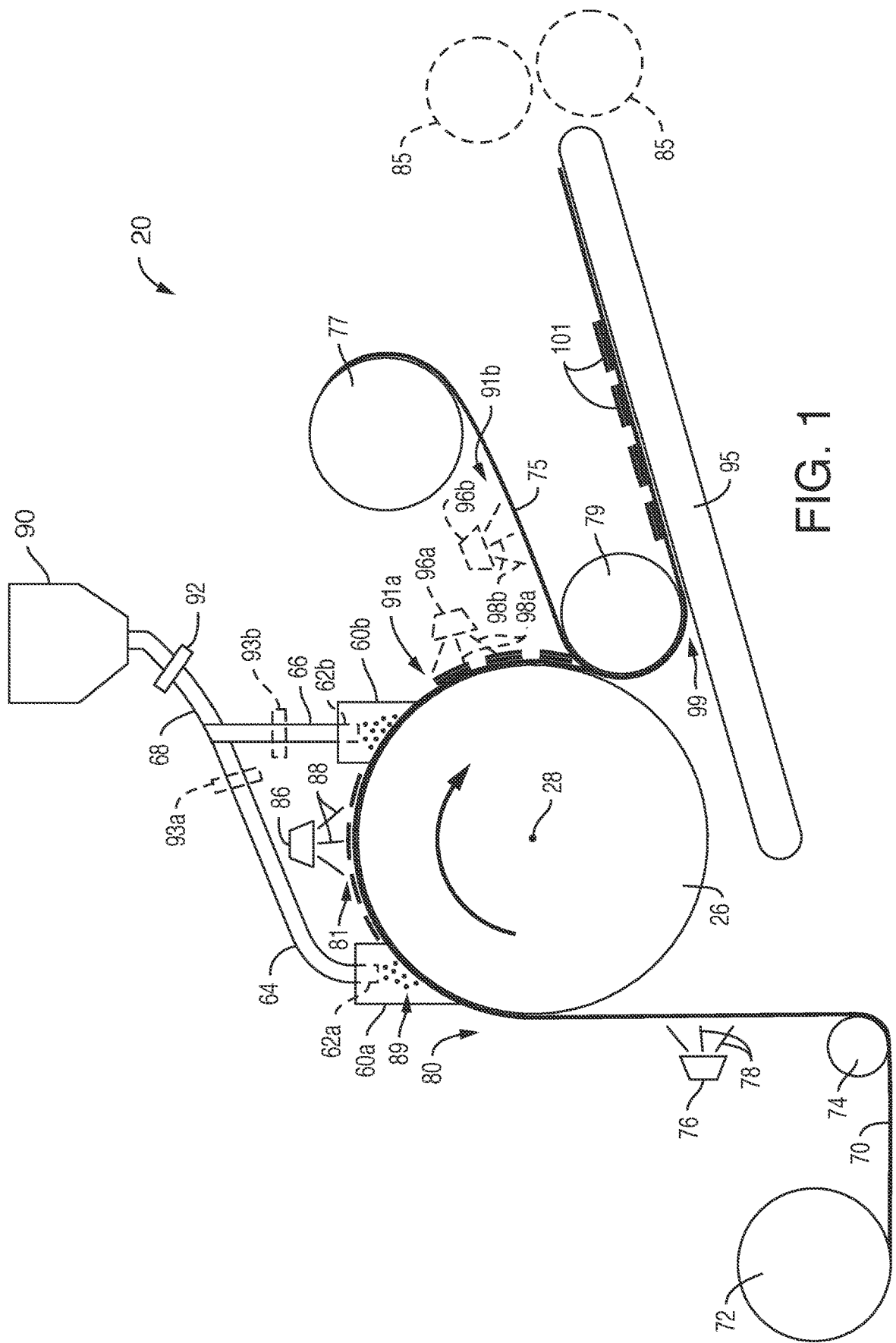
FIG. 1 is a schematic of an example forming assembly for forming absorbent cores.

With reference now to the drawings, FIG. 1 depicts a schematic drawing of an example absorbent core forming apparatus 20, which may be used to form absorbent cores. A few components of apparatus 20 include the forming drum 26 and the particulate material delivery chambers 60*a*, 60*b*. Accordingly, in some embodiments, apparatus 20 may be used to form absorbent cores comprising particulate material. Superabsorbent material (SAM) is one example of particulate material contemplated by this disclosure. In at least some of these embodiments, the particulate material content of the formed absorbent cores may comprise the majority, by weight, of the contents of the absorbent cores. In other embodiments, the particulate material content of the formed absorbent cores may comprise between 90%-100%, by weight, of the contents of the absorbent cores. These absorbent cores may be described herein as pulpless absorbent cores. As used herein, the phrase pulpless absorbent cores may include both absorbent cores that are truly pulpless and absorbent cores that are only substantially pulpless which have cellulose fibers comprising between 0.5%-10%, by weight, of the total contents of the absorbent cores. Pulpless cores may have one or more advantages relative to absorbent cores that have higher cellulose fiber content. For example, pulpless cores can have absorbent properties, such as absorbent capacity, similar to cores with higher cellulose fiber content. However, pulpless cores can have smaller dimensions than cores having cellulose fiber pulp content. In particular, the pulpless cores may have a reduced thickness in comparison to cores with higher cellulose fiber content.

In the exemplary embodiment of FIG. 1, a base carrier sheet 70 may be unwound from a carrier sheet roll 72. One or more material handling rollers 74 may be used to transport the base carrier sheet 70 proximate forming drum 26. Once in proximity to forming drum 26, the base carrier sheet 70 may be drawn to forming drum 26 by vacuum pressure, described in more detail below in relation to FIGS. 2 and 3. The forming drum 26 rotates in the direction of arrow 10, about drive-shaft 28, advancing the base carrier sheet 70 through one or more absorbent core forming stages, ultimately resulting in the absorbent cores 101. Although absorbent cores 101 are shown as discrete pads, in other embodiments, absorbent cores 101 may be formed as a continuous ribbon.

In some embodiments, the base carrier sheet 70 may comprise a nonwoven material such as a meltblown, spunbond-meltblown-spunbond (SMS), spunlace material, or a natural tissue material. However, in other embodiments, any suitable non-woven material may be used. The base carrier sheet 70 should be at least semi-permeable to air-flow. For instance, the base carrier sheet 70 should be sufficiently permeable such that air is be able to move through the base carrier sheet 70 from a top surface disposed away from the forming surface 24 to a bottom surface disposed proximate the forming surface 24, and ultimately through forming surface 24 into the interior of forming drum 26. Some example suitable dimensions of the base carrier sheet 70 include a width between about 7 cm to about 36 cm. Some example suitable basis weights for the base carrier sheet 70 range from about 5 grams per square meter (gsm) to about 50 gsm. However, the specific dimensions and basis weights used for the base carrier sheet 70 may differ, even outside of these ranges, based on the specific application or desired properties for the absorbent cores 101.

In the example of FIG. 1, the base carrier sheet 70 first moves through first adhesive application zone 80, where adhesive applicator 76 applies adhesive 78 to the base carrier sheet 70. In some examples, the adhesive 78 may be a hot-melt adhesive, such as either a contact hot-melt adhesive or a non-contact hot-melt adhesive. Although, in other examples, adhesive 78 may be any other suitable adhesive for application on a carrier sheet. Further, adhesive 78 may be applied using any suitable application technique or techniques. For instance, adhesive 78 may be applied with a spray application, with a slot-coat application, or by any other appropriate application technique.

After exiting first adhesive application zone 80, the base carrier sheet 70, now containing adhesive 78, is brought in proximity to forming drum 26, where the base carrier sheet 70 is drawn to the forming drum through vacuum pressure. The base carrier sheet then enters particulate material delivery chamber 60a. Inside of particulate material delivery chamber 60a, particulate material may be deposited onto the base carrier sheet 70. More specifically, the particulate material may be deposited onto adhesive 78, where the particulate material becomes stabilized, or immobilized on the base carrier sheet 70, by adhesive 78.

The hopper 90 in FIG. 1 may contain particulate material that is delivered to the particulate material delivery chambers 60a, 60b. The connecting pipe 68 may connect directly to the hopper 90 in order to transport the particulate material from the hopper 90 to the particulate material delivery chambers 60a, 60b. In at least some embodiments, the connecting pipe 68 may include metering device 92. The metering device 92 may be any sort of bulk material metering device, based on volumetric, gravimetric, or mass flow principles, or the like. The metering device 92 may ensure that only a specified amount (for instance, by volume or by weight) of particulate material flows through the connecting pipe per unit of time. Some example suitable ranges for the volume of particulate material flowing through the metering device 92 are between about 5,000 grams per minute (g/min) and about 25,000 g/min. In this manner, the metering device 92 can help to ensure a proper amount of particulate material is delivered to particulate material delivery chambers 60a, 60b.

In the example shown in FIG. 1, the connecting pipe 68 may split into delivery pipes 64 and 66. Each of the delivery pipes 64 and 66 may enter the particulate material delivery chambers 60a, 60b, forming particulate material delivery conduits 62a, 62b. The particulate material delivered to the particulate material delivery chambers 60a, 60b may exit the particulate material delivery conduits 62a, 62b and be deposited onto the adhesive 78 and the base carrier sheet 70. In some alternative embodiments, instead of a single metering device 92, multiple metering devices may be used to ensure proper delivery of particulate material to each of the particulate material delivery chambers 60a, 60b. For example, each of the delivery pipes 64 and 66 may include a metering device, represented by the dashed boxes 93a and 93b in FIG. 1, instead the apparatus 20 including metering device 92.

After exiting the particulate material delivery chamber 60a, the base carrier sheet 70, now containing adhesive 78 and particulate material, may enter second adhesive application zone 81. In some embodiments, second adhesive application zone 81 may be similar to first adhesive application zone 80. For example, in second adhesive application zone 81, adhesive applicator 86 may apply adhesive 88 to the base carrier sheet 70. More specifically, adhesive applicator 86 may apply adhesive 88 onto the particulate material that is stabilized on the base carrier sheet 70. In some embodiments, adhesive 88 may be the same as adhesive 78. For instance, adhesive 88 may also be a hot-melt adhesive, such as a non-contact hot-melt adhesive. Adhesive 88 may also be applied to the base carrier sheet 70 in a similar manner as adhesive 78 was applied to the base carrier sheet 70, such as with a spray application. Although, in other embodiments, adhesive 88 may be a different type of adhesive than adhesive 78 and/or may be applied in a different manner than adhesive 78.

In still other embodiments, adhesive 88 may not be a hot-melt adhesive. In some embodiments, adhesive 88 may be a spray-application aqueous binder (SAAB) adhesive. Where adhesive 88 is a SAAB adhesive, adhesive 88 may be applied with a spray-application. Implementing adhesive 88 as a SAAB adhesive may be preferable in certain embodiments, as SAAB adhesives may be able to better penetrate particulate material than hot-melt adhesives, thereby allowing for greater stabilization of the particulate material deposited onto the base carrier sheet 70.

After passing through second adhesive application zone 81, the base carrier sheet 70 now includes a first adhesive, adhesive 78, disposed on the base carrier sheet 70, a first amount of particulate material 89 (as can be seen in further detail in FIG. 6A) disposed on the adhesive 78, and a second adhesive, adhesive 88, disposed on the first amount of particulate material. The base carrier sheet 70 then enters the particulate material delivery chamber 60b. In the particulate material delivery chamber 60b, a second amount of particulate material is deposited onto adhesive 88 in a similar manner as particulate material was deposited onto adhesive 78 in the particulate delivery chamber 60a.

In some embodiments, the particulate material delivered to the base carrier sheet 70 in the particulate material delivery chambers 60a, 60b may be the same type of particulate material. In other embodiments, however, the type of particulate material delivered to the base carrier sheet 70 in the particulate material delivery chamber 60a may be different than the type of particulate material delivered to the base carrier sheet 70 in the particulate material delivery chamber 60b. In such embodiments, apparatus 20 may have two separate hoppers that each store different types of particulate material, in contrast to the example of FIG. 1. Additionally, separate connecting and delivery pipes may connect to each of the hoppers and to each of the particulate material delivery chambers 60a, 60b to maintain separation of the different particulate material types. Alternatively, apparatus 20 may still include only the single hopper 90 and the connecting and delivery pipes 68, 64, and 66, as shown in FIG. 1. In such embodiments, the hopper 90 may have two separate internal compartments to maintain separation of the different particulate material types. Additionally, connecting pipe 68 may include separate internal lumens. A first of the internal lumens may connect to a first internal compartment of the hopper 90 and to delivery pipe 64, while a second of the internal lumens may connect to a second internal compartment of the hopper 90 and to delivery pipe 66.

As mentioned previously, in some embodiments the particulate material may comprise superabsorbent material (SAM). Suitable superabsorbent materials are well known in the art and are readily available from various suppliers. Example suitable superabsorbent materials may include BASF 9700, available from BASF Corporation, a business having offices located in Charlotte, N.C., U.S.A; and Evonik 5600, available from Evonik Industries, a business having offices located in Parsippany, N.J., U.S.A.

In other embodiments, the particulate material may comprise low- or non-absorbent material such as charcoal, sugar (e.g. xylitol or the like), or encapsulated material. Accordingly, this disclosure contemplates in any of the disclosed embodiments that the delivered particulate material may be either an absorbent material, a non-absorbent material, or both. For instance, absorbent particulate material may be mixed with non-absorbent particulate material, or a first of the particulate material delivery chambers 60a, 60b may deliver absorbent particulate material and a second of the particulate material delivery chambers 60a, 60b may deliver non-absorbent particulate material.

Once the second amount of particulate material has been deposited onto the base carrier sheet 70, a top carrier sheet 75 may be applied onto the second amount of particulate material. The top carrier sheet 75 may be unwound from a roll 77 of top carrier sheet material, and may be transported proximate the forming drum 26 via one or more material handling rollers 79. After the top carrier sheet 75 has been applied onto the second amount of particulate material, the edges of the top carrier sheet 75 and the base carrier sheet 70 may be bonded together (not shown) to form the pulpless absorbent cores 101. The absorbent cores 101 may then be transported on conveyer 95 for further processing.

In some embodiments, material handling roller 79 may also perform a function similar to a nip roller. For instance, material handling roller 79 may come into close proximity to conveyer 95 in region 99 and the absorbent core 101 may be compressed to reduce bulk and/or to more securely bond the portions of the absorbent core 101 together. In other embodiments, however, one or more separate rollers may perform a nip function, such as rollers 85.

In some alternative embodiments, a third adhesive may be applied to the second amount of particulate material before the top carrier sheet 75 is applied to the second amount of particulate material. In some of these embodiments, apparatus 20 may further include third adhesive application zone 91a. Where apparatus 20 includes third adhesive application zone 91a, adhesive applicator 96a may apply adhesive 98a to the second amount of particulate material before the top carrier sheet 75 is applied. In various embodiments, adhesive 98a may be similar to either adhesive 78 or adhesive 88 described previously, and may be applied in any of the previously described methods. In different embodiments, however, apparatus 20 may include third adhesive application zone 91b instead of third adhesive application zone 91a. In these embodiments, adhesive applicator 96b may apply adhesive 98b directly to the top carrier sheet 75, instead of onto the second amount of particulate material. Additionally, adhesive 98b may be similar to either adhesive 78 or adhesive 88 described previously, except that adhesive 98b may not be a SAAB adhesive, as SAAB adhesives may not be suitable for direct application to carrier sheets. Further, adhesive 98a may be applied in any of the previously described methods. This third adhesive, applied by either adhesive applicator 96a or adhesive applicator 96b, may further help to stabilize the second amount of particulate material and/or to more securely attach the top carrier sheet 75 to the second amount of particulate material.

The adhesive applicators 76, 86, and/or 96a or 96b may be configured to apply adhesive in a continuous manner in some embodiments. In other embodiments, however, the adhesive applicators 76, 86, and/or 96a or 96b may be configured to apply adhesive in an intermittent fashion. For instance, the adhesive applicators 76, 86, and/or 96a or 96b may be applied intermittently to target zones on the base carrier sheet 70 to help stabilize the particulate material at locations on the base carrier sheet that will be most effective in absorbing liquid in the resulting absorbent cores due to the placement of the absorbent cores within an absorbent article.

Additionally, in at least some embodiments, the adhesive applicators 76, 86, and/or 96a or 96b may apply adhesive in a coordinated, intermittent fashion. In these embodiments, the adhesive applicator 86 may apply adhesive intermittently in a fashion such that the adhesive applicator 86 applies adhesive on top of the adhesive applied by adhesive applicator 76. After application of adhesive by the adhesive applicator 86, the adhesive applied by the adhesive applicator 86 would overlay the adhesive applied by the adhesive applicator 76. In embodiments that include adhesive applicator 96a or 96b, the adhesive applicator 96a or 96b may apply adhesive in an intermittent fashion such that the adhesive applied by the adhesive applicator 96a or 96b overlays the adhesive applied by the adhesive applicator 76 and the adhesive applied by the adhesive applicator 86.

Figure 2:
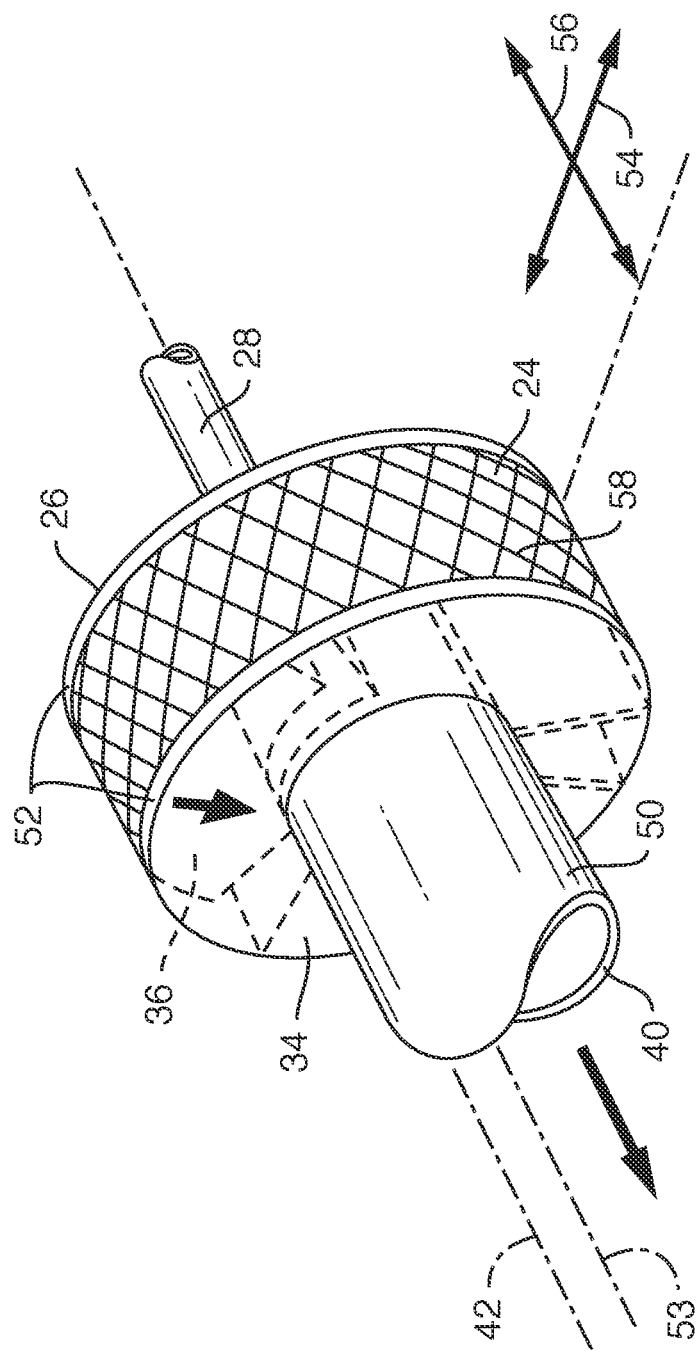
FIG. 2 is a perspective view of an exemplary forming drum that may be used in the assembly of FIG. 1.
Figure 3:
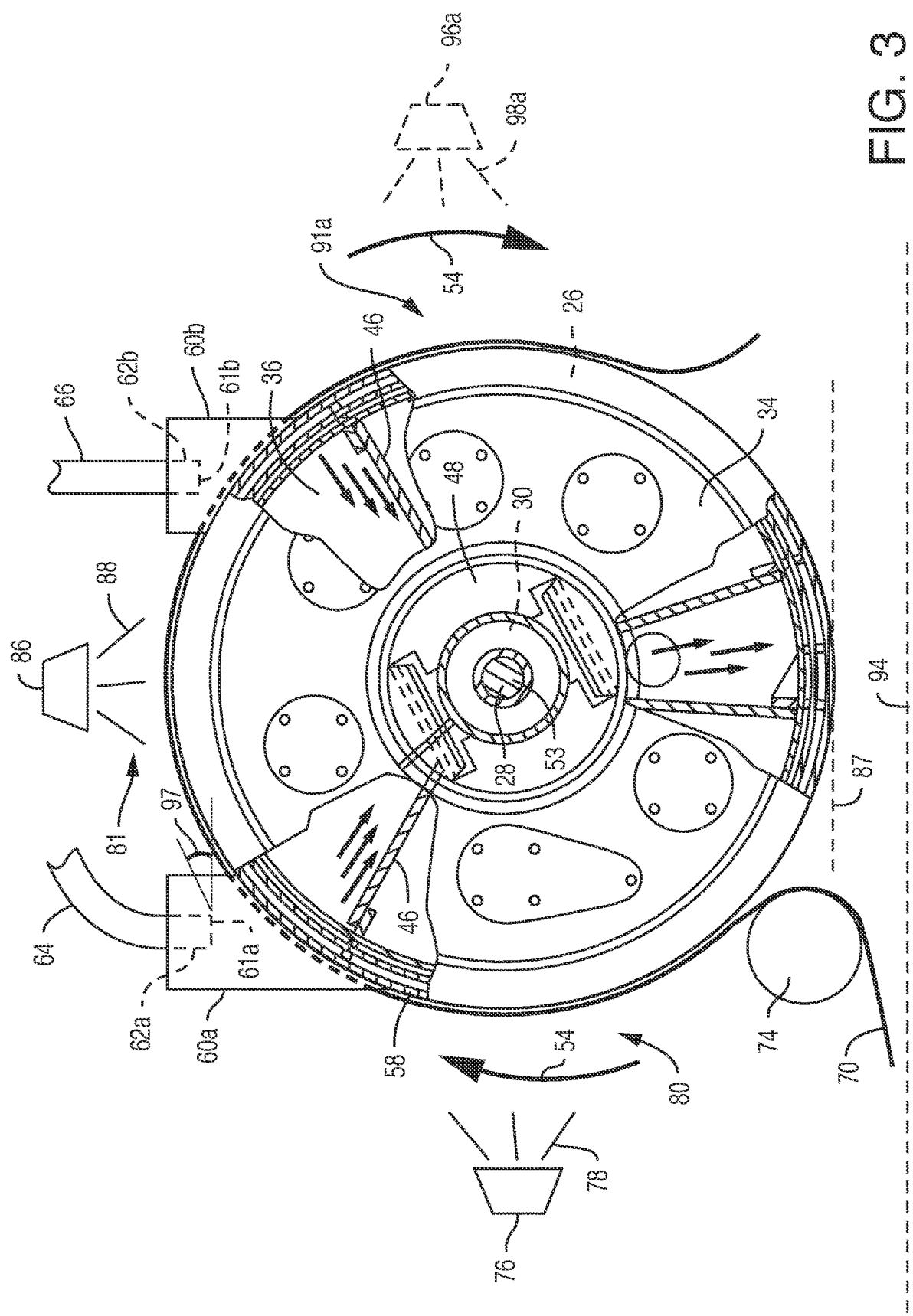
FIG. 3 is a side view of an example forming drum and associated components that may be used in the assembly of FIG. 1.

FIGS. 2 and 3 more closely depict portions of apparatus 20, including forming drum 26. The forming drum 26 includes a movable, foraminous forming surface 24, indicated by the hatched pattern in FIG. 2, extending around the circumference of the forming drum 26. The forming drum 26 is mounted on a drive shaft 28 and supported by bearings 30 (as can be seen in FIG. 3). The forming drum 26 includes a circular drum wall (not shown) operatively connected to and rotated by the drum drive shaft 28. The shaft 28 is driven in rotation by a suitable motor or line shaft (not shown) in a clockwise direction as depicted by the arrows in FIG. 3. In some embodiments, the drum wall can be a primary, load-bearing member, and the drum wall can extend generally radially and circumferentially about the drum drive shaft 28.

A vacuum duct 36 located radially inwardly of the forming surface 24 extends over an arc of the interior of the forming drum 26. The vacuum duct 36 is in fluid communication with the forming surface 24 for drawing air through the forming surface 24. The vacuum duct 36 is mounted on and in fluid communication with a vacuum supply conduit 40 connected to a vacuum source 42. The vacuum source 42 may be, for example, an exhaust fan and may create a vacuum within the forming drum which may be between about 2 inches of $H_2O$ to about 40 inches of $H_2O$. Beyond helping the base carrier sheet 70 adhere to the forming drum 26 as the base carrier sheet 70 advances around the forming drum, the vacuum pressure created by the vacuum source 42 may help to pull the particulate material exiting the particulate material delivery conduits 62a, 62b toward the forming surface 24. This vacuum pressure may help to spread the particulate material out on the forming surface 24 and to help form a more even distribution of the particulate material along the cross-machine direction 56 of the base carrier sheet 70.

The vacuum duct 36 is connected to the vacuum supply conduit 40 along an outer peripheral surface of the vacuum supply conduit 40, and extends circumferentially about at least a portion of the vacuum supply conduit 40. The vacuum duct 36 projects radially outwardly from the vacuum supply conduit 40 toward the forming surface 24 and includes axially spaced side walls 34 and angularly spaced end walls 46.

The shaft 28 extends through the drum wall and into the vacuum supply conduit 40 where it is received in the bearing 30. The bearing 30 is sealed with the vacuum supply conduit 40 so that air is not drawn in around the shaft 28 where it enters the vacuum supply conduit 40.

As representatively shown, the vacuum supply conduit 40 can include a conduit end wall 48 and a peripheral wall 50 that delimit the size and shape of the vacuum supply conduit 40. The vacuum supply conduit 40 can have any suitable cross-sectional shape. In the illustrated configuration, the vacuum supply conduit 40 has a generally circular cross-sectional shape. The vacuum supply conduit 40 can be operatively held in position with any suitable support structure. The support structure can also be joined and connected to further components or members that operatively support the portions of the vacuum supply conduit 40 structure that engage the drum drive shaft 28. For example, in the exemplary embodiment, one or more supports may connect to the bearing 30, and the entire vacuum supply conduit 40 may be supported by an overhead mount (not shown).

In the illustrated embodiment, walls 34 extend generally radially and circumferentially about the vacuum supply conduit 40. A drum rim 52 is joined to the walls 34 and is constructed and arranged to provide a substantially free movement of air through the thickness of the drum rim 52. The drum rim 52 is generally cylindrical in shape and extends along the direction of the drum axis 53, and circumferentially about the drum axis 53. As representatively shown, the drum rim 52 can be supported by and extend between the walls 34.

With reference to FIGS. 2 and 3, the forming surface 24 can be provided along the outer, cylindrical surface of the forming drum 26, and can extend along the axial and circumferential dimensions of the forming drum. The circumferential dimension is generally in a machine direction 54 and the axial dimension is generally in a cross-machine direction 56. The structure of the forming surface 24 can be composed of an assembly, and can include a foraminous member 58, which is operatively connected and joined to the forming drum 26. In some contemplated embodiments, the foraminous member 58 may be comprised of a system of multiple inserts. Exemplary foraminous members that may be used in conjunction with the present disclosure are further described in U.S. Pat. No. 6,630,088, titled "Forming media with enhanced air flow properties", filed on Oct. 23, 2000.

The forming surface 24 can be operatively held and mounted on the drum rim 52 by employing any suitable attachment mechanism. As one representative example, a system of nuts and bolts can be employed to secure the forming surface 24 onto an operative set of mounting rings. In such an example, the mounting rings can be operatively mounted on and secured to the drum rim 52. In other embodiments, the foraminous member 58 may be integral with forming drum 26.

Although not shown in FIG. 2, one or more masking plates may be attached to forming drum 26 on top of forming surface 24, as described in more detail below. The masking plates, for example, may be attached to drum rim 52, or alternately to the foraminous forming member 58. The masking plates may cover a portion of the forming surface 24 in order to block the vacuum in particular portions of the forming surface. The masking plates may allow for differently shaped absorbent cores to be formed on the forming drum 26, as will be explained in more detail below.

Suitable forming drum systems for use with the present disclosure are well known in the art. For example, see U.S. Pat. No. 4,666,647 entitled APPARATUS AND METHOD FOR FORMING A LAID FIBROUS WEB by K. Enloe et al. which issued May 19, 1987; and U.S. Pat. No. 4,761,258 entitled CONTROLLED FORMATION OF LIGHT AND HEAVY FLUFF ZONES by K. Enloe which issued Aug. 2, 1988; the entire disclosures of which are incorporated herein by reference in a manner that is consistent herewith. Other forming drum systems are described in U.S. Pat. No. 6,330,735, entitled APPARATUS AND PROCESS FOR FORMING A LAID FIBROUS WEB WITH ENHANCED BASIS WEIGHT CAPABILITY by J. T. Hahn et al. which issued Dec. 18, 2001, the entire disclosure of which is incorporated herein by reference in a manner that is consistent herewith. Systems for forming surfaces are described in U.S. Pat. No. 6,3630,088, entitled FORMING MEDIA WITH ENHANCED AIR FLOW PROPERTIES by Michael Barth Venturino et al. which issued Oct. 7, 2003, the entire disclosure of which is incorporated herein by reference in a manner that is consistent herewith.

With respect to FIG. 3, additional features of the particulate material delivery chambers 60a, 60b are evident. For instance, the particulate material delivery chambers 60a, 60b further depict the particulate material delivery conduits 62a, 62b terminating in inlets 61a, 61b. The inlets 61a, 61b, e.g. the plane of the opening of the particulate material delivery conduits 62a, 62b, may be positioned within the particulate material delivery chambers 60a, 60b such that the inlets 61a, 61b are generally parallel with ground 94 and/or with the base of the forming drum 87. In these embodiments, the particulate material delivered from the inlets 61a, 61b may exit the inlets 61a, 61b in a stream that is substantially perpendicular to the ground 94 and/or the base of the forming drum 87. Additionally, the particulate material delivery chambers 60a, 60b are both situated on the top half of the forming drum 26. In this configuration, the particulate material delivered from the particulate material delivery chambers 60a, 60b may fall with gravity towards the forming drum, instead of requiring additional energy to push the particulate material to the forming drum 26 against gravity.

However, in other embodiments, the inlets 61a, 61b may be tilted with respect to the ground 94 and/or the base of the forming drum 87. For instance, the inlets 61a, 61b may form an angle 97 with respect to the ground 94 and/or the base of the forming drum 87 (shown only with respect to inlet 61a in FIG. 3) having a value of between about 1 degree and about 45 degrees. In even further embodiments, the inlets 61a, 61b may form an angle 97 with respect to the ground 94 and/or the base of the forming drum 87 such that the inlets 61a, 61b are tangential to the forming drum 26.

Figure 4:
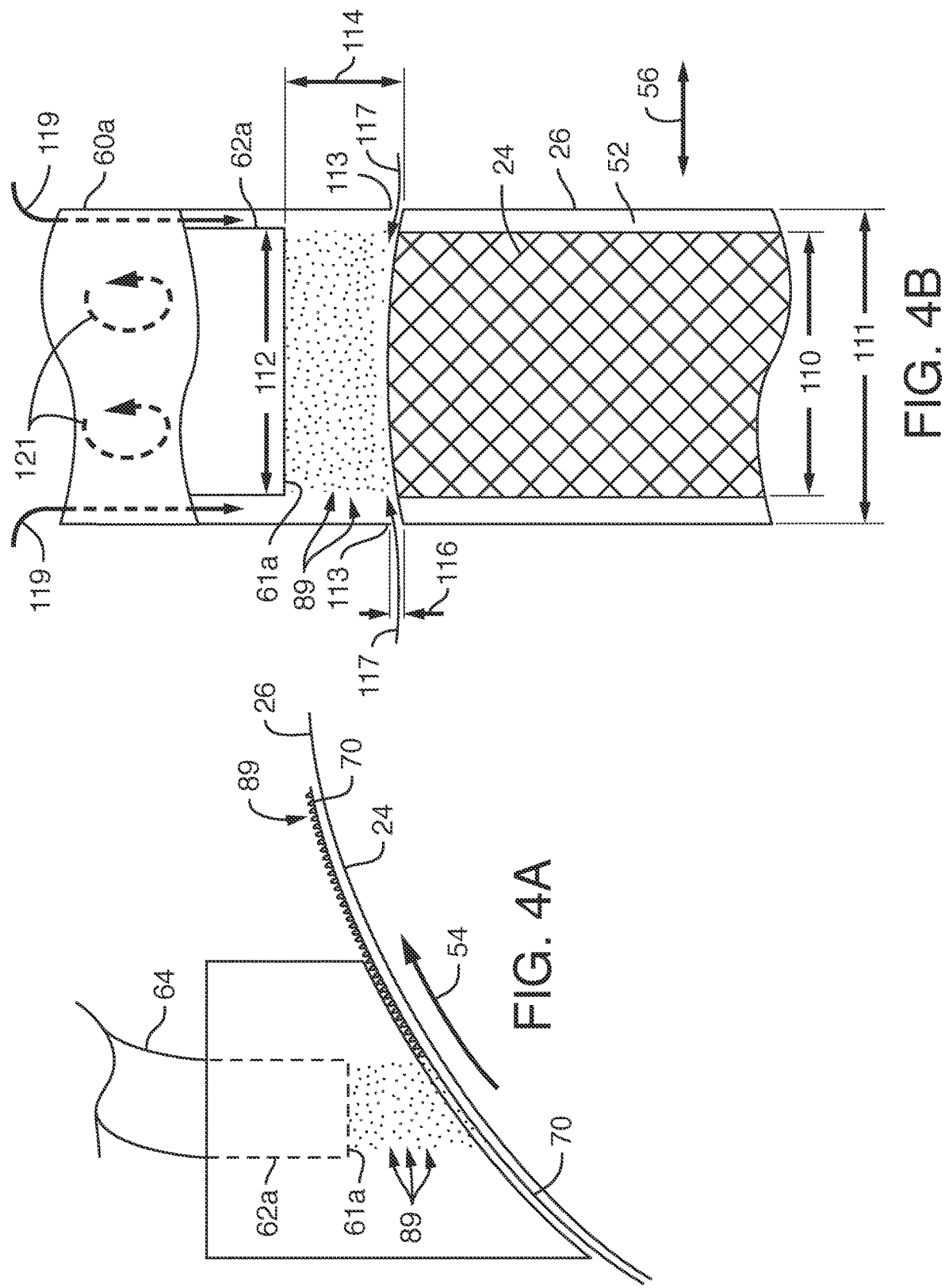
FIG. 4A is a side view of an exemplary particulate absorbent material delivery chamber that may be used in the assembly of FIG. 1.
FIG. 4B is a front view of an exemplary particulate absorbent material delivery chamber that may be used in the assembly of FIG. 1.

FIGS. 4A and 4B depict different close-up views of particulate material delivery chamber 60a. FIG. 4A depicts a close-up of particulate material delivery chamber 60a as viewed in the machine direction 54. FIG. 4A further depicts individual particulate material particles 89 exiting inlet 61a of particulate material delivery conduit 62a and being deposited onto the base carrier sheet 70. The individual particulate material particles 89 can also be seen disposed and stabilized on the portion of the base carrier sheet 70 after the particulate material delivery chamber 60a in the machine direction 54.

As mentioned previously, the particulate material may be delivered through particulate material delivery conduit 62a from the hopper 90, which results in the particulate material being gravity fed to inlet 61a. In some embodiments, the individual particulate material particles 89 exiting inlet 61a may exit with a velocity that is less than 1200 meters per minute (m/min). In other embodiments, the individual particulate material particles 89 exiting inlet 61a may exit with a velocity that is less than 900 m/min. In still other embodiments, the individual particulate material particles 89 exiting inlet 61a may exit with a velocity that is less than 600 m/min. In yet other embodiments, the individual particulate material particles 89 exiting inlet 61a may exit with a velocity that is less than 300 m/min. These velocities are in contrast to particulate material that is introduced to a forming chamber pneumatically. Where particulate material is introduced pneumatically, the minimum possible introduction velocity is over 1200 m/min, because that is the velocity at which air needs to move in order to move particulate material particles. Accordingly, gravity feeding the particulate material into the particulate material delivery chamber 60a allows the individual particulate material particles 89 to be introduced proximate the forming drum 26 with a relatively lower velocity than if the particulate material were to be pneumatically introduced. This lower introduction velocity may allow the individual particulate material particles 89 to be influenced to a greater extent by the vacuum pressure of the forming drum 26. In this manner, the apparatus 20 may be able to achieve a more even distribution of the individual particulate material particles 89 on the base carrier sheet 70 throughout the cross-machine direction 56 than if the individual particulate material particles 89 we introduced into the particulate material delivery chamber 60a pneumatically.

FIG. 4B depicts an internal view of particulate material delivery chamber 60a as viewed from the cross-machine direction 56. As can be seen in FIG. 4B, the forming drum 26 may have a drum width 110, and the forming surface 24 may have a forming surface width 111. Generally, the drum width 110 will be greater than the forming surface width 111, as the forming drum 26 will include drum rim 52. However, this is not necessary in all embodiments. FIG. 4B also depicts the forming surface 24 as a relatively uniform and continuous surface. As mentioned previously, an as will be described in more detail below, in different embodiments one or more masking plates may obscure portions of the forming surface 24.

Also shown in FIG. 4B is the particulate material delivery conduit 62a and inlet 61a having an inlet width 112. In some embodiments, the inlet width 112 may be the same as the forming surface width 111. However, in other embodiments, the inlet width 112 may be smaller or greater than the forming surface width 111. For instance, the inlet width 112 may be the same as the drum width 110. In other examples, the inlet width 112 may smaller than the forming surface width 111, such as be between about one-quarter and about nine-tenths of the forming surface width 111. Additionally, inlet width 112 may be different for each of particulate material delivery conduits 62a, 62b.

The particulate material delivery conduit 62a may further having a vertical conduit spacing 114 comprising an amount of space between the inlet 61a of the particulate material delivery conduit 62a and the forming surface 24. In some examples, the vertical conduit spacing 114 may be between about 15 cm to about 100 cm.

As shown in FIG. 4B, the particulate material delivery chamber 60a may not be sealed against the forming drum 24. For instance, there may be a gap between the bottom edges 113 of the particulate material delivery chamber 60a and the forming surface 24 or the forming drum 26. The gap may have a gap space 116 that can be between about 0.5 cm and about 5 cm. In these embodiments, air may be able to enter into the particulate material delivery chamber 60a through gap space 116, as shown by arrows 117. Entry of air into the particulate material delivery chamber 60a may push the particulate material 89 toward a center of the forming surface 24 as the particulate material falls from the inlet 61a to the forming surface 24. This may result in a cross-direction 56 width of the particulate material 89 deposited at the forming surface 24 that is less than inlet width 112. This may result in more particulate material 89 present in a central region of formed absorbent cores than if there were no gap space 116. In some alternative embodiments, gap space 116 may not be disposed between the bottom edges 113 of the particulate material delivery chamber 60a and the forming surface 26. Rather, the bottom edges 113 of the particulate material delivery chamber 60a may be sealed against the forming drum 26, and a separate hole may be disposed through a side wall of the particulate material delivery chamber 60a to allow entry of air into the particulate material delivery chamber 60a.

Accordingly, in other embodiments, there may not be a gap space 116 between the bottom edges 113 of the particulate material delivery chamber 60a and the forming surface 24 or the forming drum 26. For instance, the bottom edges 113 of the particulate material delivery chamber 60a may contact the forming surface 24 or the forming drum 26, or one or more gap fillers (not shown) may be positioned to close up the gap space 116. In these embodiments, there may be no air entering gap space 116. Accordingly, there may be no air impinging on the stream of particulate material 89 and pushing the particulate material 89 inward from the edges of the forming surface 24. In these embodiments, the cross-direction 56 width of the particulate material 89 deposited at the forming surface 24 may be close or equal to the inlet width 112.

In some additional or alternative embodiments, an upper region of the particulate material delivery chamber 60a may be open and may allow air to flow into the particulate material delivery chamber 60a as shown by arrows 119. In these embodiments, the inflow of air may cause the particulate material 89 to fall toward the forming surface 24 in a more linear path. For instance, as air enters the particulate material delivery chamber 60a, the air may be pulled toward the forming surface 24 by the vacuum pressure in the chamber 60a, and may travel in a generally linear manner. The air may pull the particulate material 89 toward the forming surface 24, and the location of the particulate material 89 deposited at the forming surface 24 may be more heavily influenced by individual starting positions of the particulate material 89 at the inlet 61a.

However, in still other additional or alternative embodiments, an upper region of the particulate material delivery chamber 60a may be sealed and may prevent air from entering the particulate material delivery chamber 60a. In these embodiments, the air within the particulate material delivery chamber 60a may be more turbulent than in the embodiments where the upper region of the particulate material delivery chamber 60a allows entry of air, as represented by arrows 121. In these embodiments, the relatively greater turbulence may cause the particulate material 89 to fall in much less linear paths and, therefore, the location of the particulate material 89 deposited at the forming surface 24 may be less dependent on their initial starting position at the inlet 61a than where the upper region of the particulate material delivery chamber 60a is open to the air. In at least some of these embodiments, the resulting formed absorbent cores may have a relatively more even distribution of particulate material 89 throughout both the cross-machine direction 56 and the machine direction 54.

Although FIGS. 4A-B only depict particulate material delivery chamber 60a, it should be understood that particulate material delivery chamber 60b may be similar to the depicted particulate material delivery chamber 60a. However, it should also be understood that contemplated embodiments of the present disclosure include apparatuses including particulate material delivery chambers 60a, 60b that differ from each other. For instance, particulate material delivery chamber 60a may include a first set of features that were described above with respect to FIGS. 4A-B, while particulate material delivery chamber 60b includes a second, different set of features. As one illustrative example, particulate material delivery chamber 60a may include an inlet, e.g. inlet 61a, that is oriented generally parallel with respect to ground 94 and/or the base of the forming drum 87 while particulate material delivery chamber 60b may include an inlet, e.g. inlet 61b, that is oriented at an angle of 45 degrees with respect to ground 94 and/or the base of the forming drum 87. Of course, this is just one example. More generally, each of the particulate material delivery chambers 60a, 60b may include any of the features described above with respect to FIGS. 4A-B, and the specific set of features of each of particulate material delivery chambers 60a, 60b may not be the same.

Figure 5:
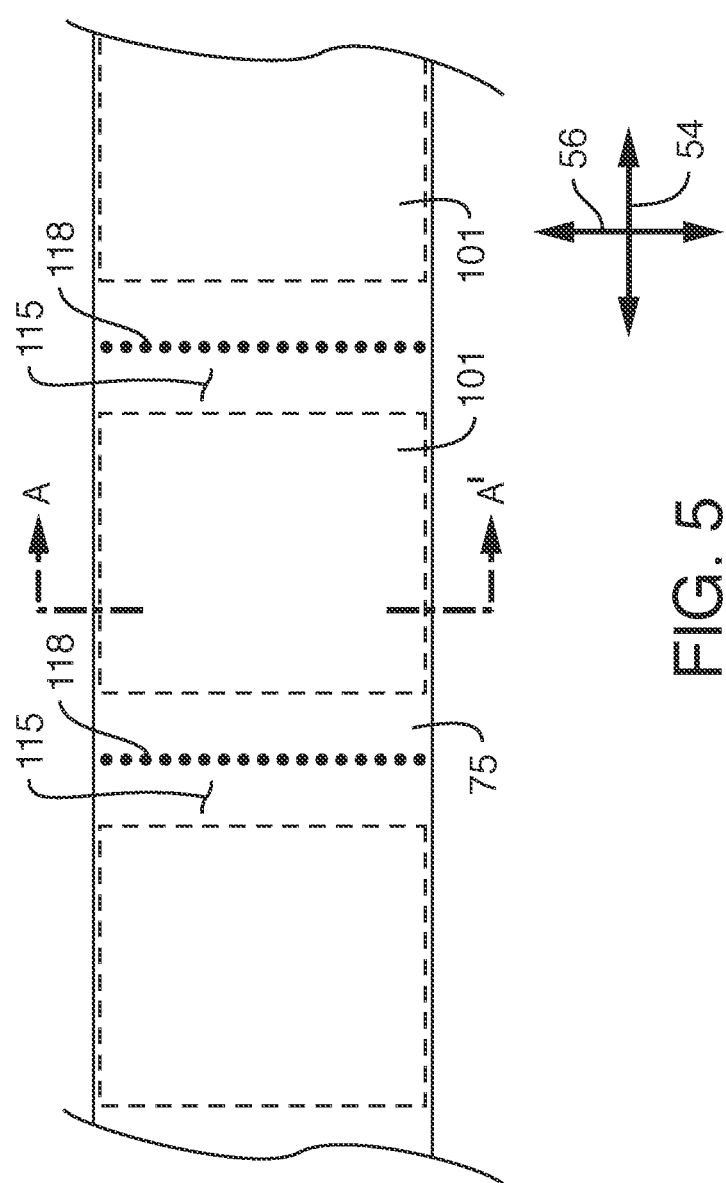
FIG. 5 is an illustration of an exemplary absorbent core structure that may be produced by the assembly of FIG. 1.

FIG. 5 depicts pulpless absorbent cores 101 as they may appear when exiting apparatus 20. In some examples, the absorbent cores 101 may be formed on a continuous carrier sheet, for instance the base carrier sheet 70 as shown in FIG. 1. As the base carrier sheet 70 including the various adhesives and particulate material exit off of the forming drum 26, another continuous carrier sheet, for instance the top carrier sheet 75, may be applied over the top of the base carrier sheet 70. In this manner, a continuous length of absorbent core may be formed by apparatus 20. However, as mentioned previously, in some embodiments, the forming surface 24 may include one or more masking members which may block a portion of the forming surface 24. In such embodiments, portions of the resulting length of the absorbent core may include gaps where there is no, or relatively little, particulate material content. These gaps are represented by gap regions 115 in FIG. 5. As the absorbent cores 101 were being formed on the forming surface 24, the applied vacuum would have been blocked by the masked portions of the forming surface such that little to no particulate material would have been drawn to the base carrier sheet 70 in gap regions 115. Accordingly, in such embodiments, discrete absorbent cores 101 may be formed on the continuous base carrier sheet 70, as shown in FIG. 5. The base carrier sheet 70 and the top carrier sheet 75 may later be cut, for instance along cut lines 118, in order to form separated absorbent cores. In at least some embodiments, a knife roll may be used to cut the base carrier sheet 70 and the top carrier sheet 75 into separated absorbent cores.

Figure 6A:
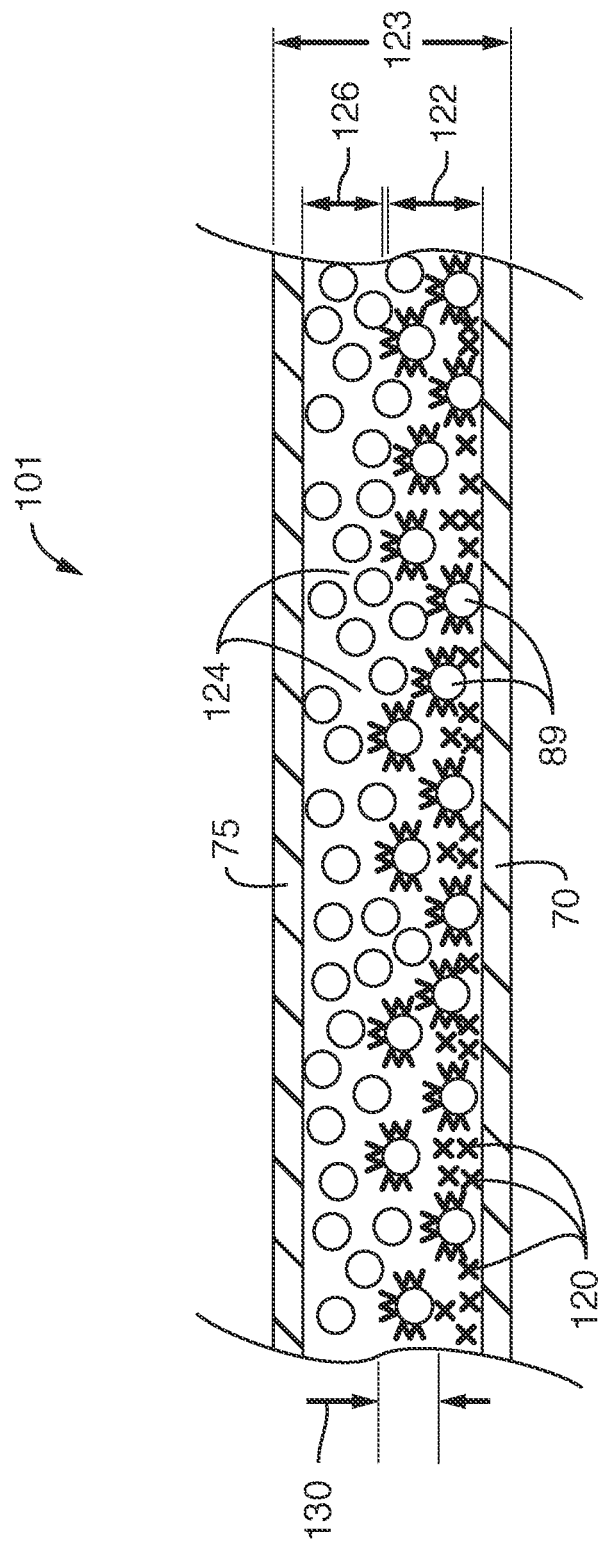
FIG. 6A is a cross-section view of an exemplary absorbent core that may be produced by the assembly of FIG. 1.

FIG. 6A depicts an example cross-section of an absorbent core 101 taken along line A-A' in FIG. 5. In the example of FIG. 6A, the absorbent core 101 was formed using only two adhesives. For instance, the absorbent core 101 of FIG. 6A includes the base carrier sheet 70. On top of the base carrier sheet 70 is the first adhesive 120, represented by the 'x's. The first adhesive 120, in some embodiments, may comprise and adhesive such as adhesive 78 described with respect to FIG. 1. Adhesive 120 may have been applied to the base carrier sheet 70, for instance, in the first adhesive application zone 80 of FIG. 1.

On top of the first adhesive 120 is the first amount of particulate material 122, represented by particulate material particles 89. The first amount of particulate material 122 may have been applied to the first adhesive 120, for example, in the particulate material delivery chamber 60a of FIG. 1. The first amount of particulate material 122 may have a thickness of between about 0.1 mm and about 1 mm.

On top of the first amount of particulate material 122 is the second adhesive 124, represented by the 'w's. The second adhesive 124, in some embodiments, may comprise an adhesive such as adhesive 88 described with respect to FIG. 1. The second adhesive 122 may have been applied to the first amount of particulate material 122, for instance, in the second adhesive application zone 81 of FIG. 1.

On top of the second adhesive 124 is the second amount of particulate material 126. The second amount of particulate material 126 may have been formed, for example, in the particulate material delivery chamber 60b of FIG. 1. The second amount of particulate material 126 may have a thickness of between about 0.1 mm and about 1 mm. Finally, the top carrier sheet 75 is shown disposed on top of the second amount of particulate material 126.

In some embodiments, some of the adhesive 124 may penetrate into the first amount of particulate material 122. For instance, in the example of FIG. 6A, strands of the first adhesive 124 (as represented by the 'w's) are shown penetrating the first amount particulate material 122 a distance 130. In some examples, distance 130 may range from between about 0.1 mm to about 1 mm. Generally, where the adhesive 124 is a SAAB adhesive, the distance 130 may be on the higher end of the range, as SAAB may be more effective at penetrating the first amount of particulate material 122 than other types of adhesives, such as hot-melt adhesive. The greater penetration distance of SAAB may allow for relatively greater stabilization of the particulate material 89 than other types of adhesive that have lesser penetrating ability.

Figure 6B:
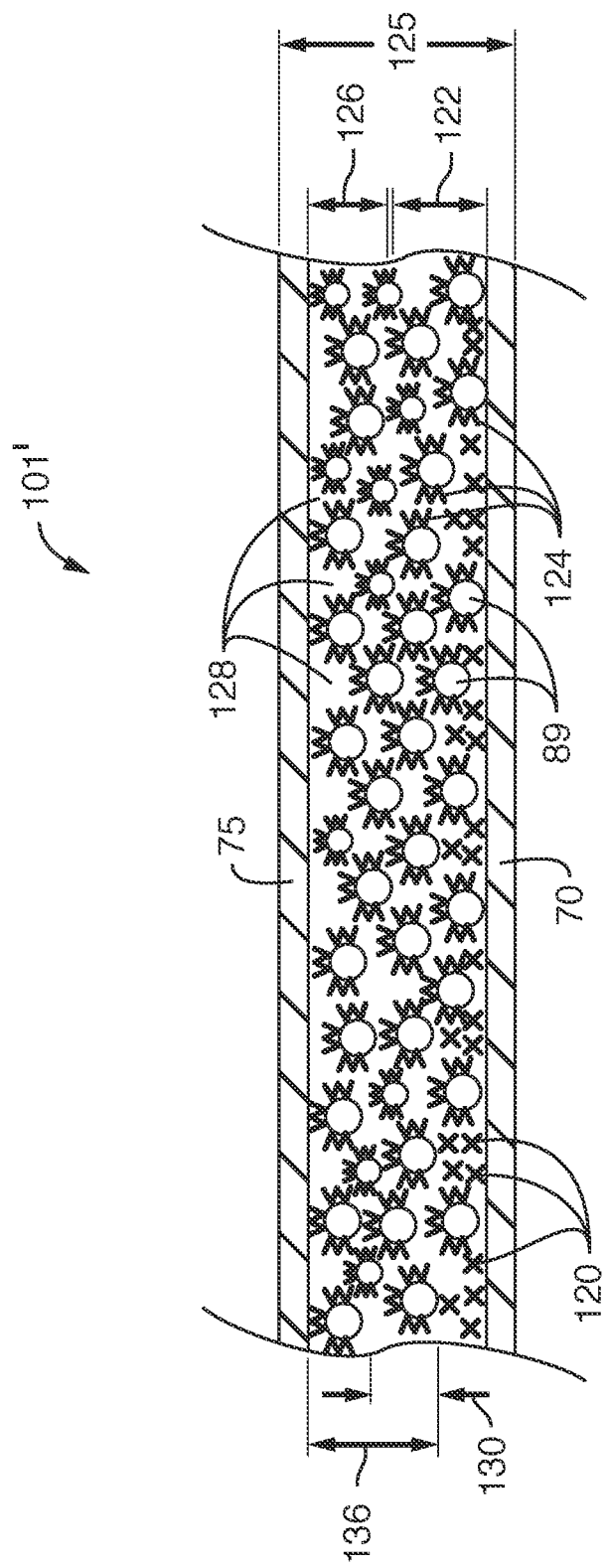
FIG. 6B is a cross-section view of an alternative exemplary absorbent core that may be produced by the assembly of FIG. 1.

FIG. 6B depicts an example cross-section of an alternative absorbent core 101' taken along line A-A' in FIG. 5. In the example of FIG. 6B, the absorbent core 101' was formed using three separate adhesive applications. For instance, the absorbent core 101' of FIG. 6B may be the same as the absorbent core 101 of FIG. 6A except that the absorbent core 101' of FIG. 6B further includes third adhesive 128, which is also represented by 'w's. This is because in the embodiment of FIG. 6B, the second adhesive 124 and the third adhesive 128 are the same adhesive, such as a SAAB adhesive, but may have been applied in separate process steps.

The third adhesive 128, in some embodiments, may comprise adhesive 98a of FIG. 1. In these examples, the third adhesive 128 may have been applied to the second amount of particulate material 126 in the third adhesive application zone 91a. As with the second adhesive 120, the third adhesive 128 may penetrate at least partially into the particulate material 89. The penetration distance of the third adhesive 120 is shown by penetration distance 136, which may range from about 0.1 mm to about 2 mm. In at least some embodiments, the third adhesive 128 may penetrate throughout the entire laminate structure of absorbent core 101'.

In other embodiments, however, the third adhesive 128 may not be the same as the second adhesive 124. For instance, in at least some contemplated embodiments, the third adhesive may be applied to the top carrier sheet 75 rather than the second amount of particulate material 126. In these embodiments, the third adhesive may be a hot-melt adhesive rather than a SAAB adhesive, as SAAB adhesives may not be suitable for application to carrier sheets. Accordingly, the third adhesive 128 may be applied to the top carrier sheet such as in third adhesive application zone 91b of FIG. 1 instead of in third adhesive zone 91a.

In general, as shown in FIGS. 6A and 6B, absorbent cores 101 and 101' may have overall thicknesses 123, 125, respectively. Some suitable values for thicknesses 123, 125 range from between about 0.2 mm to about 2.0 mm. However, as will be described in more detail with respect to FIG. 8, the processes described herein may further include additional applications of adhesive and of particulate material, forming even larger laminate structures.

In even further additional or alternative embodiments, one or more tissue or other non-woven sheets may be interspersed between the adhesives and particulate material of the absorbent cores 101, 101'. With specific respect to FIG. 6A, for instance, in some embodiments an intermediate tissue or other non-woven material (not shown) may be placed on top of the first amount of particulate material 122. Then, the second amount of particulate material 126 may be deposited onto that intermediate tissue or other non-woven material. In further embodiments, an adhesive may then be applied to the laminate structure, as shown in FIG. 6B. Although only shown with two separate application of particulate material, as will be described in more detail with respect to FIG. 8, contemplated absorbent cores may include any suitable number of applications of particulate material. Accordingly, in such embodiments, an intermediate tissue or other non-woven sheet may be disposed between each adjacent application of particulate material.

Figure 7:
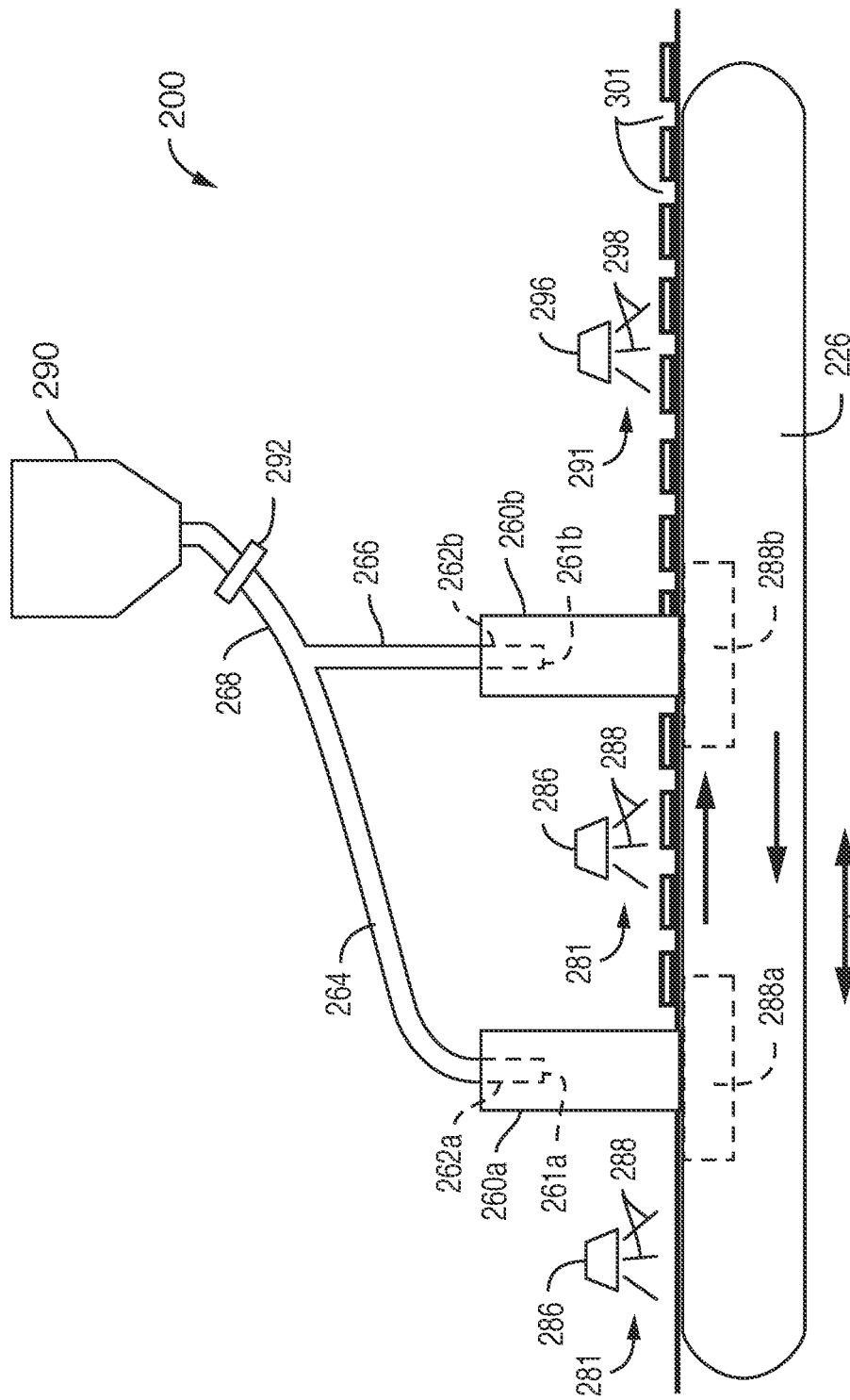
FIG. 7 is an alternative schematic of an example forming assembly for forming absorbent cores.

FIG. 7 depicts an alternative pulpless absorbent core forming apparatus 200. Pulpless absorbent core forming apparatus 200 may generally be similar to apparatus 20, except that instead of using a forming drum, pulpless absorbent core forming apparatus 200 uses a planer forming conveyer 226. Although the apparatus 200 may be slightly different from the apparatus 20, the method of forming pulpless absorbent cores with the apparatus 200 is very similar to the process described with respect to apparatus 20. For instance, the base carrier sheet 270 is first fed onto the forming conveyer 226. The base carrier sheet 270 then encounters adhesive application zone 281, where adhesive applicator 276 applies adhesive 278 to the base carrier sheet 270.

Next, the base carrier sheet 270 may enter particulate material delivery chamber 260a. Particulate material may be delivered to the particulate material delivery chamber 260a from the hopper 290 through connecting pipe 268 and delivery pipe 264. Delivery pipe 264 may enter the particulate material delivery chamber 260a and form particulate material delivery conduit 262a. The particulate material delivered to the particulate material delivery conduit 262a ultimately exits the particulate material delivery conduit 262a through inlet 261a. In some embodiments, a metering device 292 may be present to meter out a specific amount of particulate material from the hopper 290 to ensure a predetermined amount of particulate material flows to particulate material delivery conduit 262a.

Additionally, in at least some of these embodiments, a vacuum chamber 228a may be present under the forming conveyer. For instance, the forming conveyer may have a foraminous forming surface (not shown) and air may be able to move across the foraminous forming surface. In the region of vacuum chamber 228a, air may be moving from within the particulate material delivery chamber 260a through the foraminous forming surface and into a duct (not shown) coming out of the forming conveyer 226. This movement of air may pull particulate material exiting inlet 261a toward the forming conveyer to be deposited onto the adhesive 278 and the base carrier sheet 270 forming a layer comprising a first particulate material. Although vacuum ducts 228a and 228b are shown only in the vicinity of the particulate material delivery chambers 260a, 260b, in other embodiments, vacuum chambers 228a, 228b may extend outside of the region around the particulate material delivery chambers 260a, 260b and over a greater extent of the forming conveyer 226 than is shown in FIG. 7.

After exiting the particulate material delivery chamber 260a, the base carrier sheet 270, now including adhesive 278 and a first amount of particulate material, encounters adhesive application zone 281. Within adhesive application zone 281, an adhesive applicator 286 applies adhesive 288 onto the first amount of particulate material that was deposited onto adhesive 278 and the base carrier sheet 270 within the particulate material delivery chamber 260a.

The base carrier sheet 270 may then enter the particulate material delivery chamber 260b. Particulate material may be delivered to the particulate material delivery chamber 260b through connecting pipe 268 and through delivery pipe 266. Delivery pipe 266 may enter the particulate material delivery chamber 260b and form particulate material delivery conduit 262b, which in turn may end at inlet 261b. Particulate material delivered from the hopper 290 may exit inlet 261b and be drawn toward the adhesive 288 due to vacuum chamber 228b. Ultimately, a second amount of particulate material may be deposited onto the adhesive 288.

Further processing steps may be included to ultimately form pulpless absorbent cores 301. For instance, in some embodiments, a top carrier sheet (not shown) may be applied over the second amount of particulate material. Additionally, a third adhesive zone 291 may be included where adhesive applicator 296 applies a third adhesive, adhesive 298 onto the second amount of particulate material, or, alternatively, onto the top carrier sheet before the top carrier sheet is applied to the second amount of particulate material. In still further embodiments, the resulting pulpless absorbent cores may be further processed, for example by delivery through a nip roller, or separation by a knife roll. Generally, any of the additional or alternative process steps described with respect to apparatus 20 may also be implemented with respect to apparatus 200.

Figure 8:
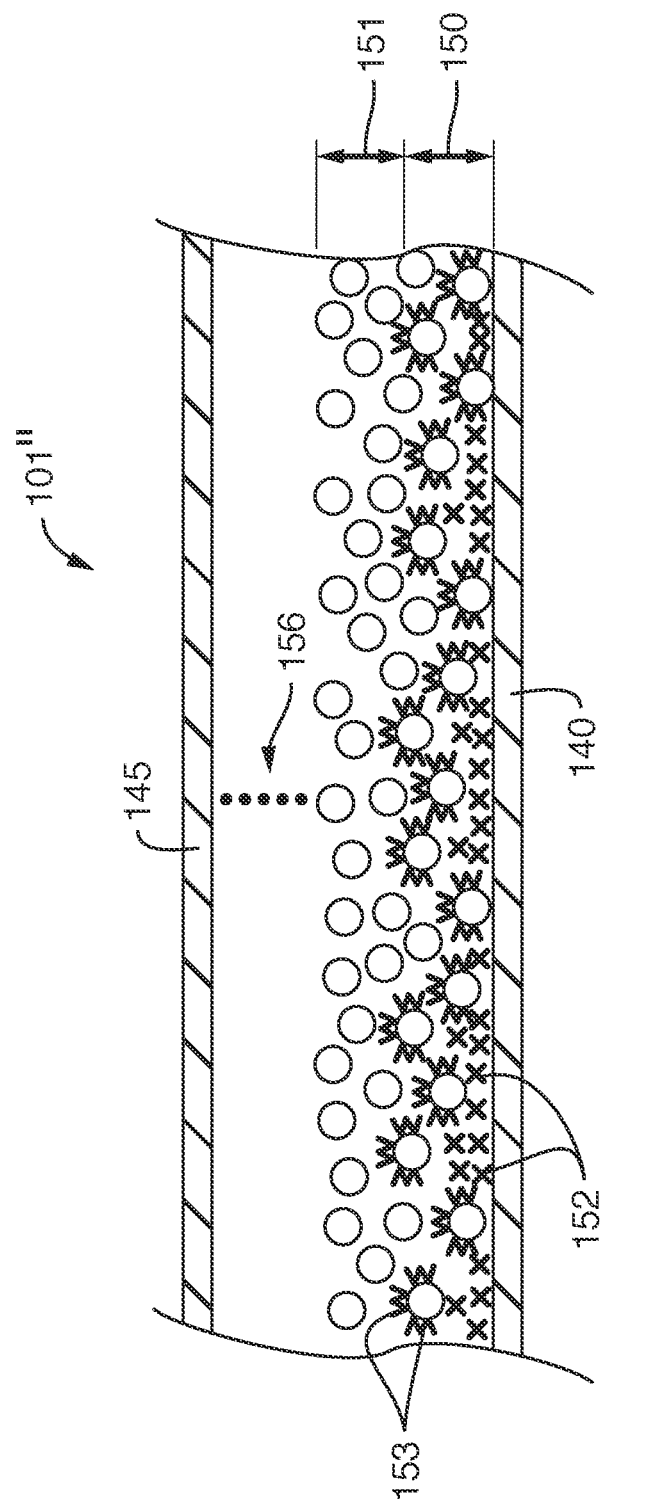
FIG. 8 is a cross-section view of an alternative exemplary absorbent core that may be produced by the assembly of FIG. 1 or FIG. 7.

In further alternative embodiments, it should be understood that the pulpless absorbent cores contemplated by this disclosure are not limited to only two particulate material applications. For instance, FIG. 8 depicts a generic pulpless absorbent core 101" that may be formed according to the techniques disclosed herein and having any suitable number of particulate material applications. The pulpless absorbent core 101" includes a base carrier sheet 140, a top carrier sheet 145, and a first amount of particulate material 150 and a second amount of particulate material 151. The pulpless absorbent core 101" further includes a first adhesive 152 and a second adhesive 153. The adhesives 152, 153 and the first and second amounts of particulate material 150, 151 may be applied in a manner similar to that described with respect to apparatus 20 or 200.

However, pulpless absorbent core 101" may be formed from any suitable number of additional adhesive and particulate material applications. For instance, each pair of an additional application of adhesive and another amount of particulate material may be thought as a unit building up the absorbent core 101". Accordingly, apparatus 20 or 200 may be modified to include additional adhesive application zone and particulate material delivery chamber units situated after second adhesive application zone 81 and particulate material delivery chamber 60b or adhesive application zone 281 and particulate material delivery chamber 260b. For each additional adhesive application zone and particulate material delivery chamber unit, pulpless absorbent core 101" may include another adhesive and amount of particulate material. Although the pulpless absorbent core 101" is contemplated to include any number of suitable additional units of adhesive and particulate material, as indicated by dots 156, some example suitable number of adhesive and particulate material units include 3, 4, 5, 6, and 7.

Figure 9:
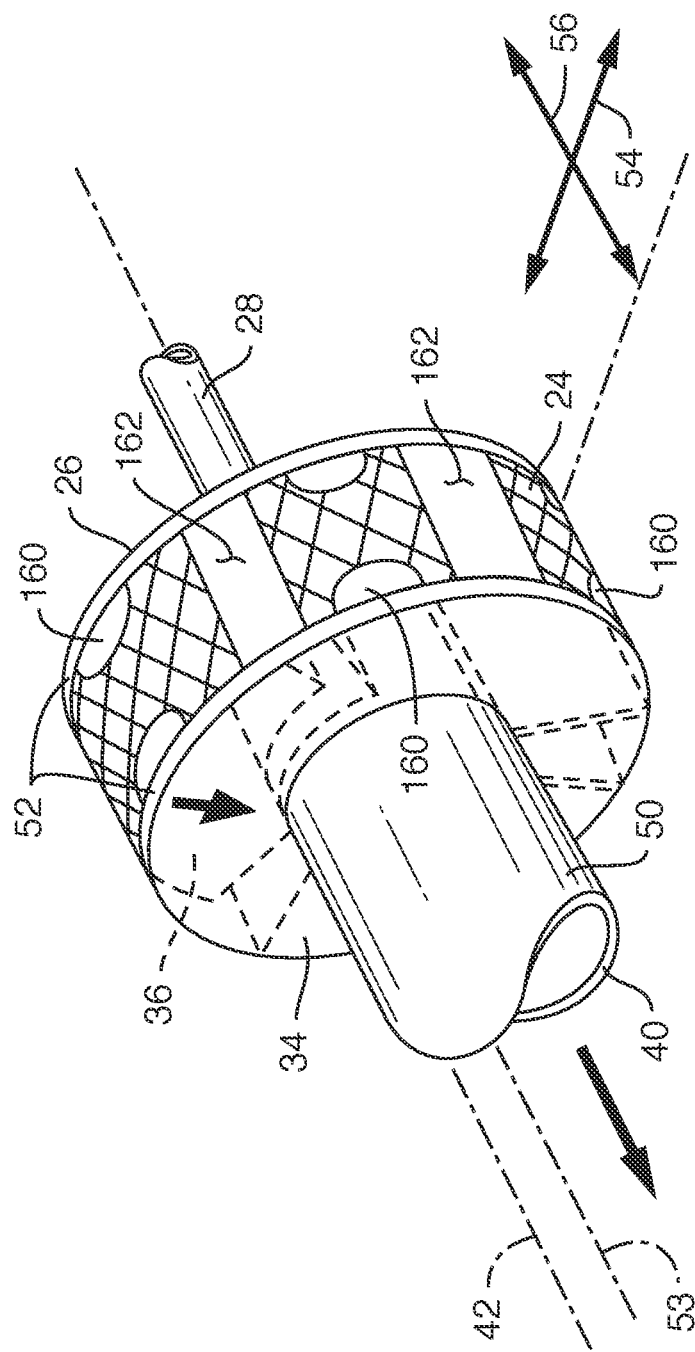
FIG. 9 is a perspective view of a forming drum including a plurality of masking members for forming shaped absorbent cores.

As mentioned previously, in some embodiments, one or more masking members may be used in order to form shaped pulpless absorbent cores. FIG. 9 depicts forming drum 26 including example masking members 160, although similar masking members may be used with forming conveyer 226. Masking members 160 mask portions of the forming surface 24, creating a pattern of shaped un-masked areas of the forming surface 24. These shaped un-masked areas will affect a distribution of particulate material within the resulting absorbent cores, thereby helping to create the shaped absorbent cores.

Figure 10:
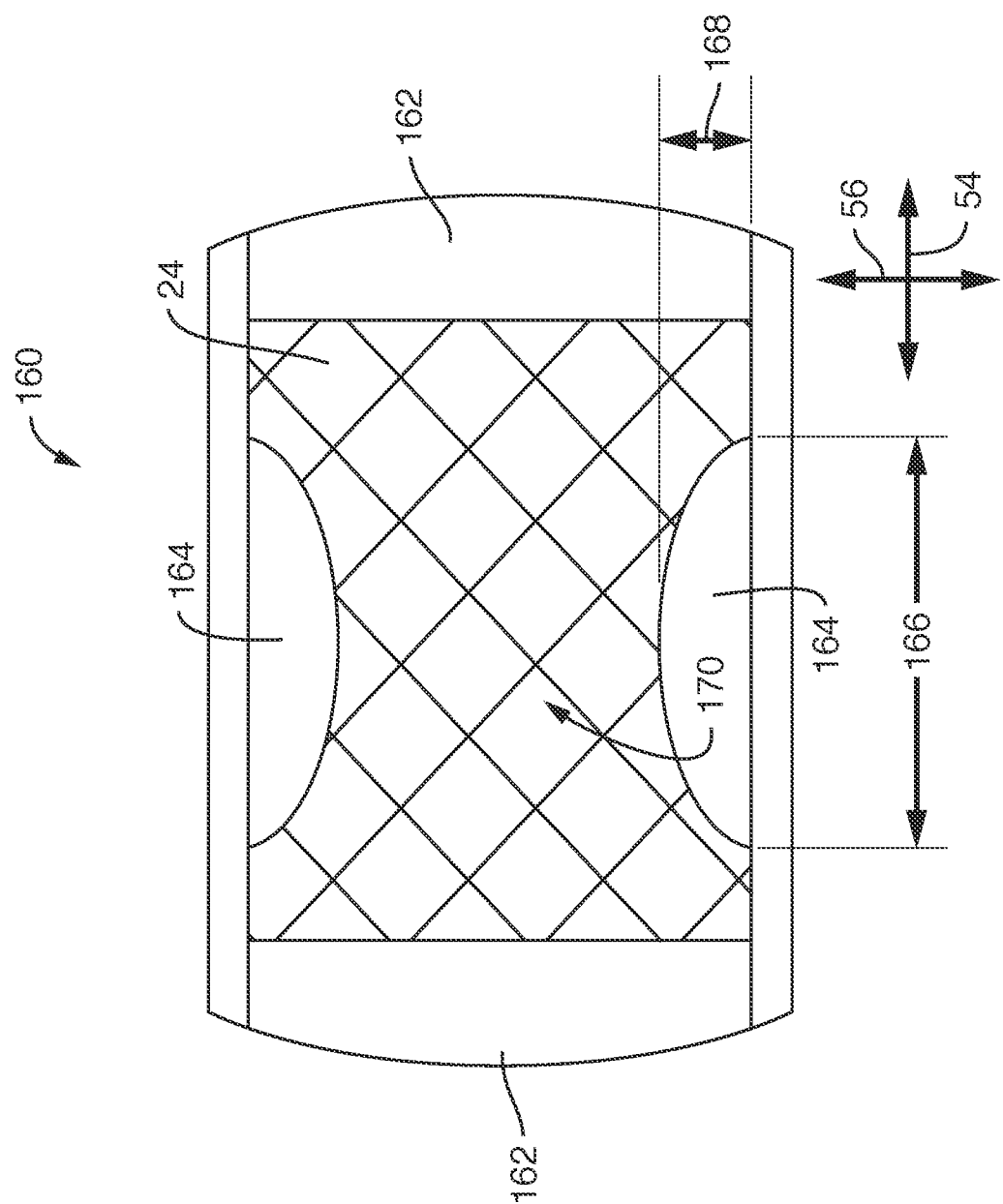
FIG. 10 is a top view of a masking member disposed on the forming drum of FIG. 9.

Although only shown with one example shape in FIGS. 9 and 10, in other suitable embodiments, the masking members 160 can have any number of different patterns. In still further embodiments, each of the masking members 160 can have different patterns and may be arranged in any order on the forming drum 26. The illustrated system of masking members 160 in FIG. 9 includes substantially identical masking members 160 arranged consecutively around the circumference of the forming drum 26. The masking members 160 can be joined and assembled to the forming drum 26 and/or the forming surface 24 by employing any conventional attaching or mounting mechanisms. For example, the masking members 160 may be secured to the forming surface 24 by a plurality of bolts inserted through holes in the masking members 160 and the forming surface 24.

The masking members 160 may have any shape suitable for mounting onto the forming surface 24. For example, the masking members 160 may have an outer perimeter that forms a substantially rectangular shape. Additionally, the masking members 160 may have a slight curve along their length in the machine direction 54 to form an arc for fitting on the cylindrical forming surface 24. In other suitable embodiments, the masking members 160 may be substantially flat for fitting on planar forming surfaces, such as the planer forming conveyer 226 of apparatus 200. The curve of each masking member 160 may have a radius substantially equal to the radius of the forming surface 24 such that the masking members 160 fit on the forming surface 24. When joined together, a series of masking members 160 can completely concentrically encircle the circumference of the forming surface 24.

FIG. 10 depicts a close-up of one exemplary masking member 160 disposed over the forming surface 24. As can be seen in FIG. 10, masking member 160 includes both masking end portions 162 and masking side portions 164. Masking side portions 164 may extend along the masking member 160 for a distance 166. Some example values of distance 166 may range from about 10 cm to about 30 cm. Additionally, masking side portions 164 may extend inward from the edges of the masking member 160 a distance 168. Some example values of distance 168 may range from about 1 cm to about 5 cm. The masking side portions 164 may act to form a crotch region 170 in the resulting formed absorbent cores.

When the masking members 160 are used within the processes described with respect to apparatus 20 and apparatus 200, the masking members 160 may affect a distribution of particulate material within a resulting absorbent core. As described previously, as the base carrier sheet travels around the forming drum 26, the base carrier sheet may be drawn to the forming surface 24 by the use of a vacuum drawing air through forming surface 24 and into an interior of the forming drum 26. Additionally, as the base carrier sheet travels through a particulate material delivery chamber, the particulate material may be drawn to the base carrier sheet by the vacuum. Where masking members 160 are used, the base carrier sheet travels around the forming drum 26 on top of the masking members 160, which effectively block air moving through the forming surface 24 in the masked areas. Accordingly, as the base carrier sheet travels through a particulate material delivery chamber, the particulate material will be drawn preferentially onto the base carrier sheet over the un-masked areas of the forming surface 24.

Figure 11:
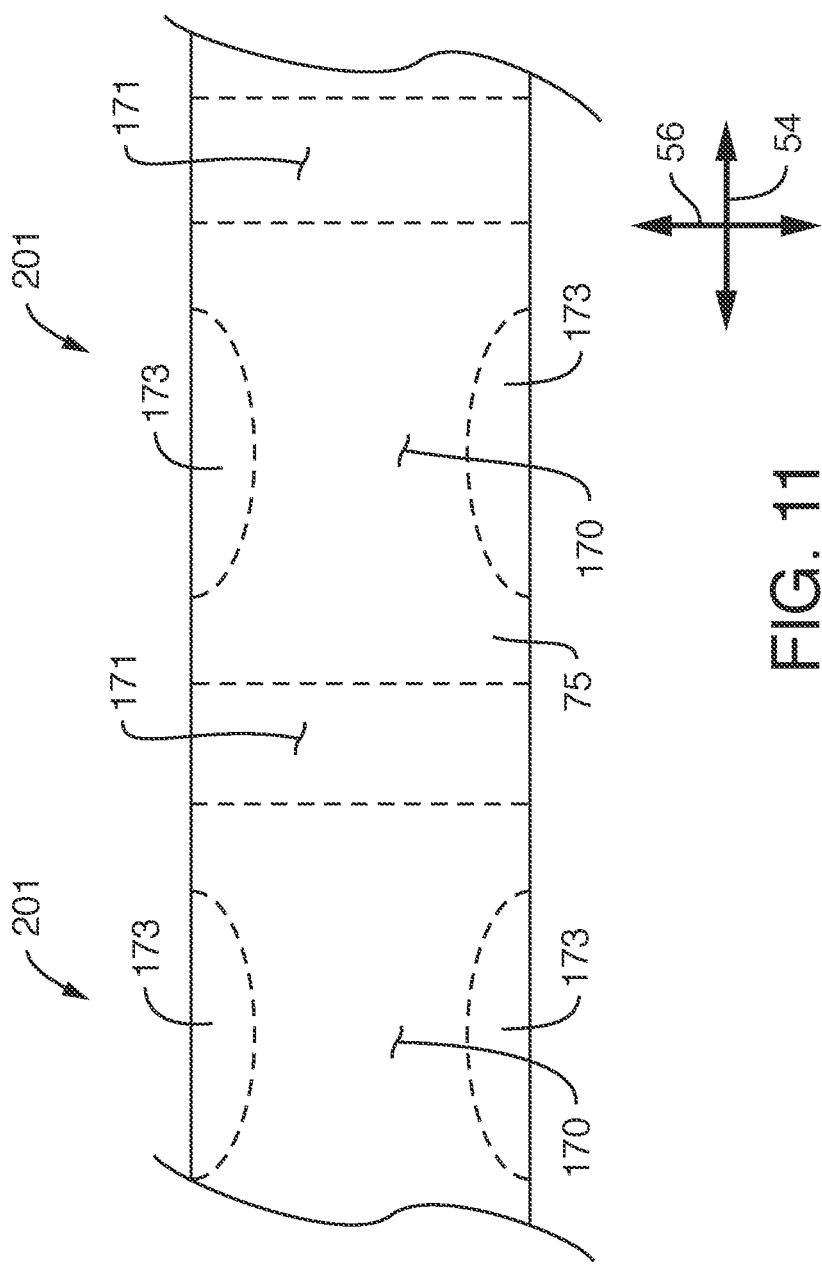
FIG. 11 is an illustration of an exemplary shaped absorbent core structure that may be produced using the forming drum and masking members of FIGS. 9 and 10.

FIG. 11 depicts example shaped absorbent cores 201 that may be formed using the masking members 160. In the example of FIG. 11, different regions of the shaped absorbent cores 201 are shown with dashed lines. The shaped absorbent cores 201 may include regions of relatively higher average basis weights, such as within the crotch regions 170 and other regions where the forming surface 24 was un-covered by the masking members 160. The shaped absorbent cores 201 may also include regions of relatively lower average basis weights, such as in end regions 171 and leg regions 173. In embodiments contemplated by this disclosure, the areas of relatively higher average basis weights may have average basis weights ranging from between about 100 grams per meter (gsm) to about 1000 gsm. The areas of relatively lower average basis weights may have average basis weights ranging from between about 50 gsm to about 400 gsm. In some embodiments, the shaped absorbent cores 201 may be separated into individual shaped absorbent cores by cutting the length of resulting shaped absorbent cores 201 in the end regions 171.

The shaped absorbent cores 201 formed using masking members, such as masking members 160, may have some benefits over non-shaped absorbent cores. For instance, the regions of lower basis weights of particulate material may allow the shaped absorbent cores 201 to have a lower overall particulate material content than non-shaped cores, resulting in lower manufacturing costs. However, because of the locations of the areas of higher basis weights, overall absorption performance of the shaped absorbent cores 201 may be at least the same as corresponding non-shaped absorbent cores.

Figure 12:
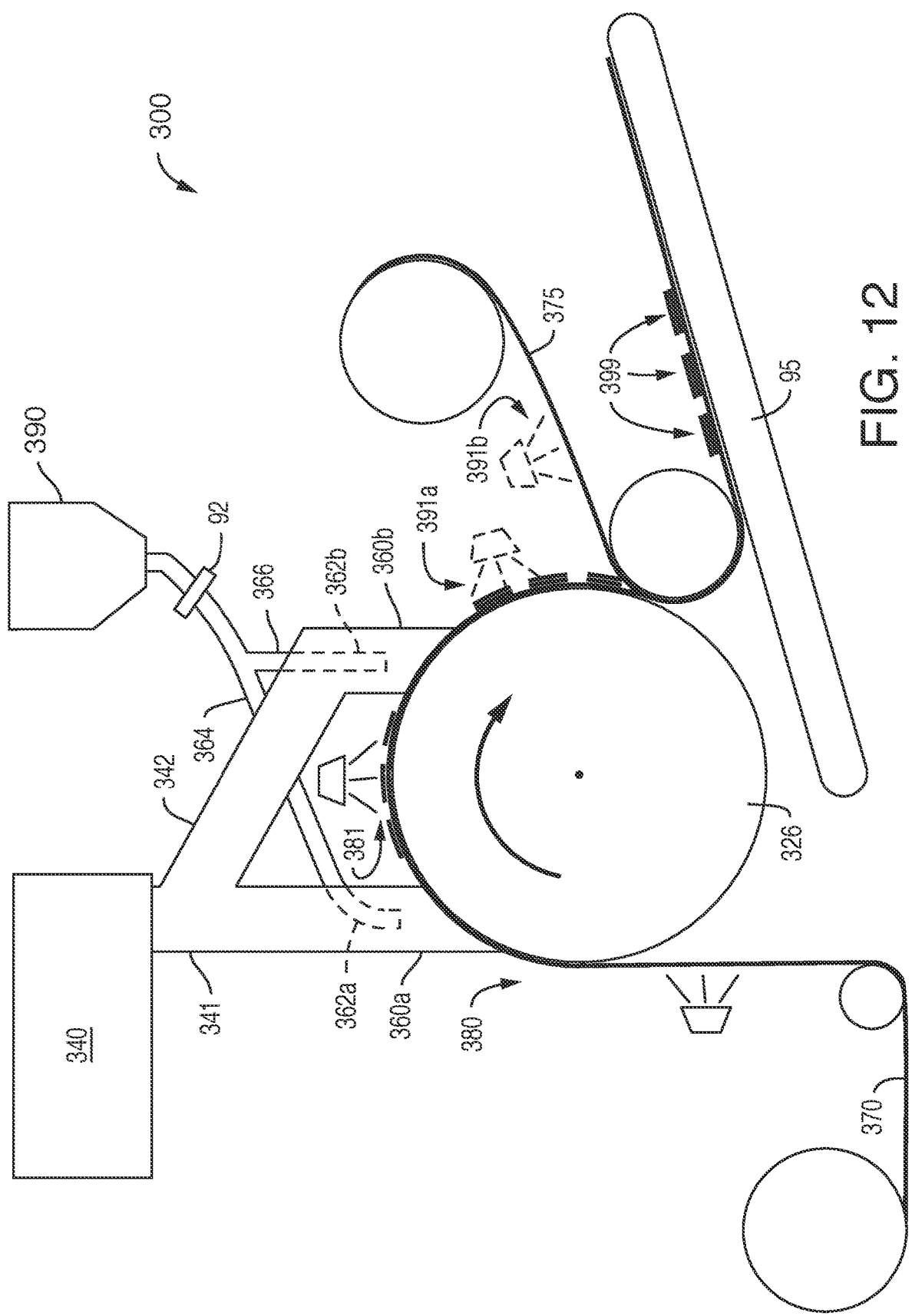
FIG. 12 is a schematic of an example forming assembly for forming absorbent cores including both pulp fluff and particulate absorbent material.

As mentioned previously, the pulpless absorbent cores of the present disclosure may be truly pulpless, or the pulpless absorbent cores may have a relatively small pulp content. For example, some of the pulpless absorbent cores of the present disclosure may include an amount of cellulose fibers that is between about 0.5% and about 10%, by weight, of the total contents of the cores. The addition of a small amount of cellulose fibers to the absorbent cores the present disclosure may impart a greater feeling of softness or provide other beneficial properties to the absorbent cores. FIG. 12 depicts one example apparatus, apparatus 300, which may be used to form the pulpless absorbent cores that have a small pulp content.

Apparatus 300 is very similar to apparatus 20 of FIG. 1. For instance, a base carrier sheet 370 may be fed onto forming drum 326. The base carrier sheet 370 may then advance through a series of adhesive applications zone 380, 381 (and, possibly 391a or 391b) and particulate material delivery chambers 360a, 360b. A top carrier sheet 375 may then be applied to form the resulting absorbent cores 399.

One difference between apparatus 20 and apparatus 300 is that apparatus 300 may further include fiberizer 340. In the embodiment of FIG. 12, the fiberizer 340 may be fed pulp or cellulose sheets and break up the cellulose sheets into many individual fibers. The fiberizer 340 may be a hammer mill-type fiberizer, or any other suitable type of fiberizer known in the art. The cellulose fibers may exit the fiberizer 340 into delivery ducts 341 and 342. The delivery ducts may ultimately form material delivery chambers 360a, 360b.

The material delivery chambers 360a, 360b may differ from the particulate material delivery chambers 60a, 60b of apparatus 20 in that the material delivery chambers 360a, 360b may deliver both particulate material and cellulose fibers to the base carrier sheet. For example, cellulose fibers may travel through the delivery ducts 341, 342 and enter the material delivery chambers 360a, 360b. Gravity, along with the vacuum pressure within the material delivery chambers 360a, 360b will cause the cellulose fibers to deposit onto the base carrier sheet 370.

Particulate material may also be delivered to the material delivery chambers 360a, 360b. For instance, particulate material may be stored in hopper 390 and may be delivered to the material delivery chambers 360a, 360b through delivery pipes 364, 366. The delivery pipes 364, 366 may ultimately form particulate material delivery conduits 362a, 362b within the material delivery chambers 360a, 360b. The delivered particulate material may exit the particulate material delivery conduits 362a, 362b within the material delivery chambers 360a, 360b. Similar to the pulp fibers, gravity and the vacuum pressure within the material delivery chambers 360a, 360b will cause the particulate material to be deposited onto the base carrier sheet 370. In this manner, apparatus 300 may be used to form pulpless absorbent cores containing an amount of cellulose fibers representing between about 0.5% and about 10% of the total weight of the materials within the pulpless absorbent cores.

Figure 13:
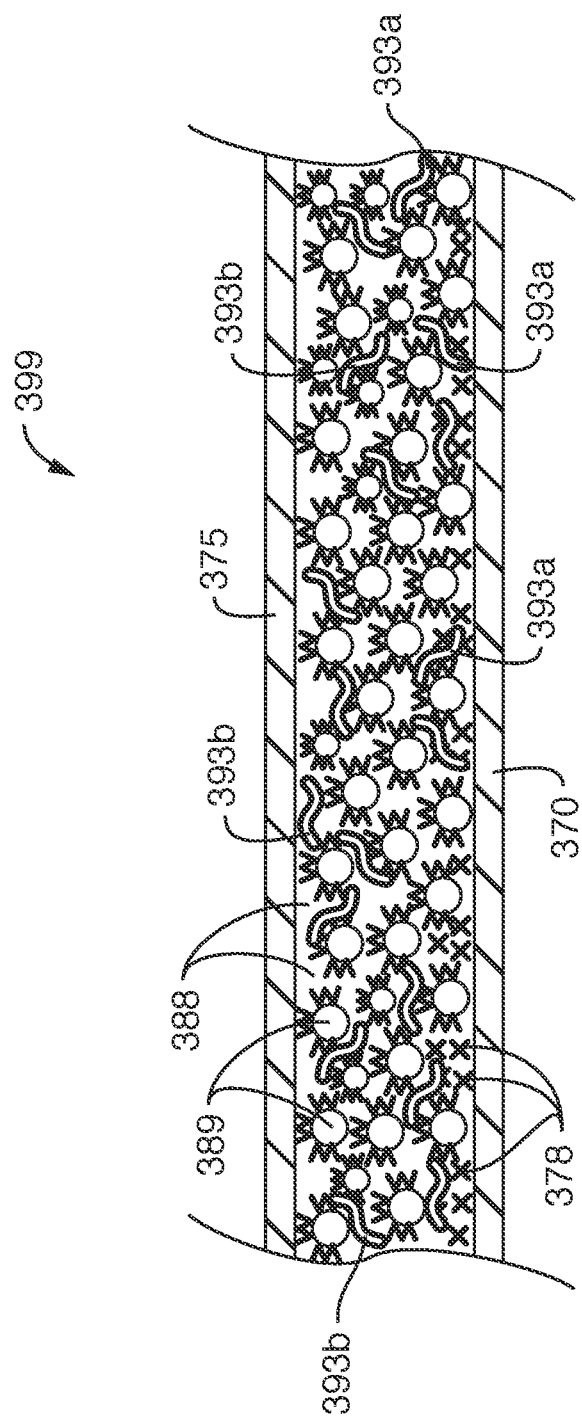
FIG. 13 depicts a cross-section of an exemplary absorbent core that may for formed by the forming assembly of FIG. 12.

FIG. 13 depicts a cross-section of an example absorbent core 399 that may be formed by the apparatus 300. FIG. 13 depicts absorbent core 399 including base carrier sheet 370 and top carrier sheet 375. Absorbent core 399 also includes adhesives 378 and 388, represented by 'x's and 'w's, respectively. In general, the absorbent core 399 may be similar to, and may be formed similarly to, the other absorbent cores of the present disclosure, such as absorbent cores 101, 101', and 101". Unlike the previous absorbent cores, however, absorbent core 399 further includes cellulose fibers 393a, 393b. As can be seen, cellulose fibers 393, 393b are disposed intermixed with the individual particulate material particles 389. Cellulose fibers 393a may be deposited, for instance, along with a first amount of particulate material particles 389, such as in particulate material delivery chamber 360a of FIG. 12. Cellulose fibers 393b may be deposited, for instance, along with a second amount of particulate material particles 389, such as in particulate material delivery chamber 360b of FIG. 12. As mentioned previously the addition of cellulose fibers may impart a greater softness to absorbent cores of the present disclosure, and the cellulose fibers may further help to stabilize the particulate material particles 389 between the base carrier sheet 370 and the top carrier sheet 375.

Again, it should be understood that FIG. 12 only represents one contemplated embodiment. In further embodiments, apparatuses 20 and/or 200 may be modified to include only a single particulate material delivery chamber that further intermixes cellulose fibers with the particulate material before deposition at a forming surface, instead of the two shown with respect to FIG. 12. In general, the apparatuses 20 and/or 200 may include a number of particulate material delivery chambers that allow for the intermixing of cellulose fibers and particulate material that is less than all of the particulate material delivery chambers of the apparatuses. In these alternative embodiments, then, a relatively smaller proportion of the formed absorbent cores may include cellulose fibers. For instance, if the cellulose fibers were intermixed with a first amount of particulate material, the mixture of cellulose fibers and particulate material may be located proximate the base carrier sheet. However, if the cellulose fibers were intermixed with a second (or third, fourth, etc.) amount of particulate material, the mixture of cellulose fibers and particulate material may be located closer to the top carrier sheet than the first amount of particulate material.

In alternative embodiments, instead of forming the pulpless absorbent cores of the present disclosure with both a base carrier sheet and a top carrier sheet, as described previously, some contemplated methods may only use a single carrier sheet. FIGS. 14A and 14B depict example embodiments where a single carrier sheet may be used instead of both a base carrier sheet and a top carrier sheet.

FIG. 14A depicts carrier sheet 405. In some embodiments, carrier sheet 405 may have a first edge region 402 having a first edge 403 and a second edge region 406 having a second edge 407, with a middle region 404 disposed between the first edge region 402 and the second edge region 406. In the embodiment of FIG. 14A, particulate material and adhesive may only be applied within the middle region 404. After application of adhesive and particulate material, instead of applying a second carrier sheet as described herein previously, the second edge region 406 may be folded over the middle region 404 and onto the first edge region 402 such that the second edge 407 is disposed proximate the first edge 403. The edges 403, 407 may then be bonded together to create an enclosed pulpless absorbent core. Bonding the edges 403 and 407 together may be done by any suitable method, such as by pressure bonding, adhesive bonding, ultrasonic bonding, or the like. The apparatuses described herein may be modified to produce such pulpless absorbent cores. For instance, instead of machinery to apply the top carrier sheets, the apparatuses described herein may include folding and bonding machinery, which are well known in the art, to fold the second edge region 406 onto the first edge region 402 and to bond the regions 402, 406 together.

In some embodiments according to FIG. 14A, the carrier sheet 405 may have a width 410. Width 410 may be greater than twice the width of a forming surface used to create pulpless absorbent cores, or alternatively greater than twice the width of an un-masked portion of a forming surface used to create pulpless absorbent cores. In some specific examples, width 410 may range between about 25 cm and about 60 cm.

The middle region 404 may have a width 412. The width 412 may range from between about 40% to about 50% of the overall width 410 of the carrier sheet 405. Additionally, the first edge region 402 may have a width 414 that is be between about 0.5% and about 10% of the overall width 410 of the carrier sheet 405.

FIG. 14B depicts another example embodiment of a single carrier sheet that may be used to form the pulpless absorbent cores of the present disclosure. In the example of FIG. 14B, the carrier sheet 450 may have an overall width 460. The overall width 460 may have values similar to those described with respect to width 410. Additionally, the carrier sheet 450 may have a first edge region 452, a middle region 454, and a second edge region 456. As with the embodiment of FIG. 14A, adhesive and particulate material may only be applied to the carrier sheet 450 within the middle region 454. After application of adhesive and particulate material to the middle region 454, one of the first edge region 452 or the second edge region 456 may be folded over onto the middle region 454. Then, the other of the first edge region 452 or the second edge region 456 may be folded over the middle region 454. In some embodiments, the edge regions 452, 456 may overlap over the middle region 454, and at least a portion of each of the first edge region 452 and the second edge region 456 may be bonded together to form an enclosed pulpless absorbent core.

Similarly to carrier sheet 405, in some embodiments the width 460 of the carrier sheet 450 may be greater than twice the width of a forming surface used to create pulpless absorbent cores, or greater than an un-masked portion of a forming surface used to create pulpless absorbent cores. However, this is not necessary in all embodiments. In at least some embodiments, width 460 may range between about 25 cm and about 60 cm.

The region 454 of the carrier sheet 450 may have a width 462. The width 462 may range from between about 33% to about 50% of the overall width 460 of the carrier sheet 450. In some embodiments, each of the first edge region 452 and the second edge region 456 may have a width (not shown) that is between about 25% and about 33% of the overall width 460. However, the widths of the first edge region 452 and the second edge region 456 do not necessarily need to be equal. For example, the width of the first edge region 452 may be between about 35% and about 40% of the overall width 460 and the width of the second edge region 456 may be between about 10% and about 25% of the overall width of 460, or vice versa.

Figure 15B:
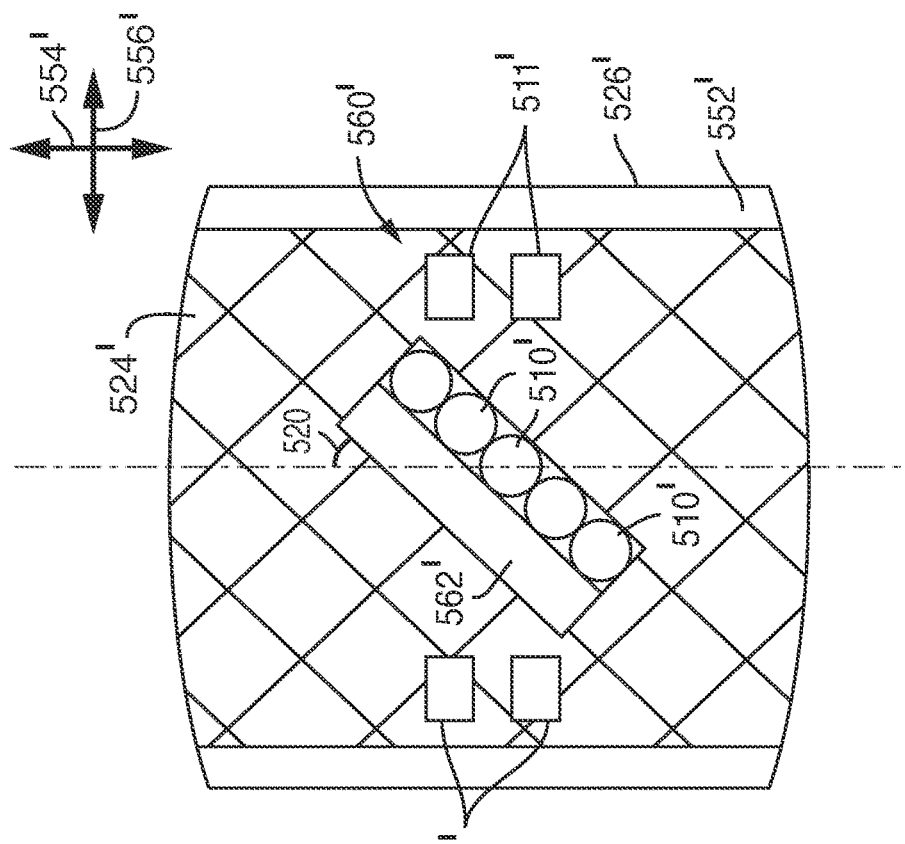
FIGS. 15A and 15B depict top-down internal schematic views of exemplary components that may be used to form a matrix layer of particulate absorbent material and adhesive.

In at least some alternative embodiments, instead of depositing particulate material and adhesive in discrete steps, the apparatuses disclosed herein may be modified to deposit one or more matrix layers, with each matrix layer comprising a combination of particulate material and adhesive. For instance, FIGS. 15A and 15B depict top-down exemplary schematics of machinery that may be used with the various apparatuses described herein to form a matrix layer within an absorbent core.

Figure 15A:
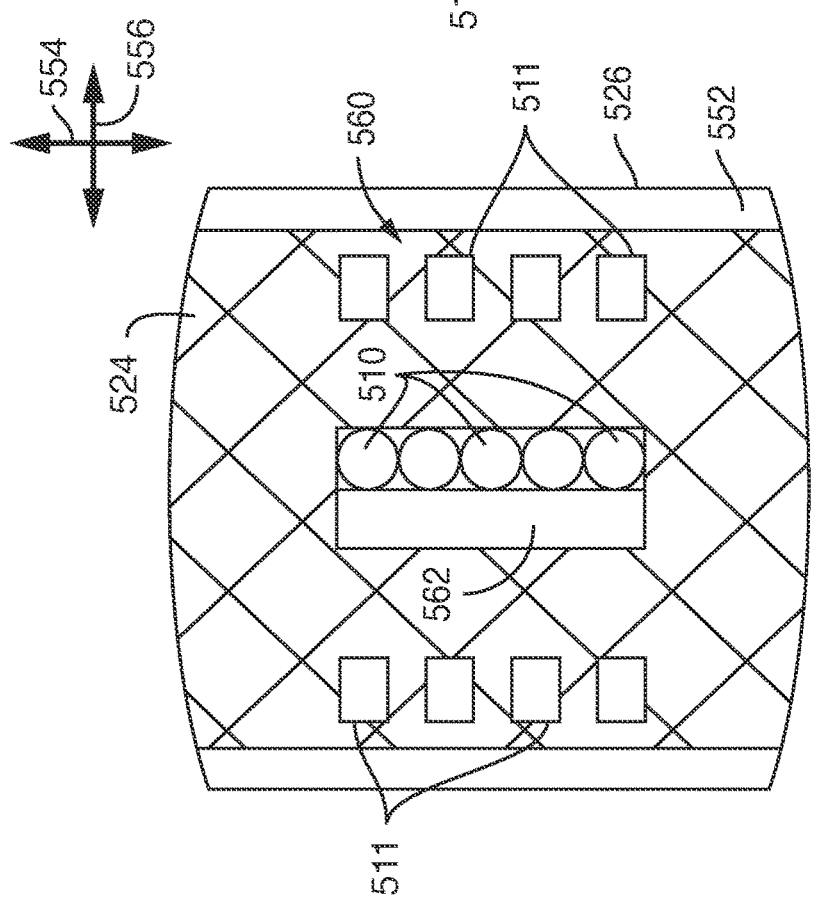

FIG. 15A depicts exemplary forming drum 526. The forming surface 524 is depicted disposed on the forming drum 526 extending between the drum rims 552. Particulate material delivery conduit 562 is also shown in FIG. 15A. FIG. 15A further depicts adhesive application nozzles 510 and air blowers 511. In some embodiments, the particulate material delivery conduit 562 and the adhesive application nozzles 510 may be disposed within an overall chamber (not shown in FIG. 15A), for example a particulate material delivery chamber as described herein, but this is not necessary in all embodiments.

As shown in FIG. 15A, the particulate material delivery conduit 562 can generally extend for a length in a machine direction 554 that is greater than a width that the particulate material delivery conduit 562 extends in a cross-machine direction 556. Additionally, the particulate material delivery conduit 562 may generally be disposed over a center region of the forming surface 524. Some example lengths for the particulate material delivery conduit 562 range from between about 10 cm to about 100 cm. Some example widths for the particulate material delivery conduit 562 range from between about 15 cm to about 50 cm.

Disposed adjacent to the particulate material delivery conduit 562 are one or more adhesive application nozzles 510. The adhesive application nozzles 510 may be configured to deliver adhesive into particulate material as the particulate material falls from the particulate material delivery conduit 562 toward the forming surface 524. When particulate material is delivered from the particulate material delivery conduit 562, and adhesive delivered from the adhesive application nozzles 510, the particulate material and the adhesive intermix as they fall toward the forming surface 524. As the particulate material and the adhesive are deposited at the forming surface 524, the particulate material and the adhesive form a matrix of particulate material and adhesive, as described in more detail below.

In some embodiments, the adhesive application nozzles 510 may be configured to provide a generally continuous stream of adhesive, while in other embodiments one or more of the adhesive application nozzles 510 may be configured to alternatingly be turned "on" and "off" to provide discontinuous streams of adhesive through one or more of the adhesive application nozzles 510. Although depicted as five separate adhesive application nozzles 510, in other embodiments, additional or fewer adhesive application nozzles 510 may be used. In different embodiments, the number of adhesive application nozzles 510 may range from between about five to about twenty.

Air blowers 511 are optional components and, where present, may generally be disposed on either side of the particulate material delivery conduit 562/adhesive application nozzles 510, or on both sides as shown in FIG. 15A. In the example of FIG. 15A, the air blowers 511 may be disposed a distance 512 from the particulate material delivery conduit 562 and a distance 514 from the adhesive application nozzles 510. The distance 512 may range between about 1 cm and about 10 cm. The distance 514 may range between about 3 cm and about 8 cm.

Where present, the air blowers 511 may deliver air jets at predetermined velocities, sufficient to urge the adhesive streams from at least some of the adhesive application nozzles 510 inward and toward the center of the substrate the forming surface 524, either continuously or for periodic intervals. The periodic intervals may be effected by periodically switching one or more of the air blowers 511 "on" and "off," by periodically blocking or diverting the jets of air from the air blowers 511 so that the jets of air do not manipulate the adhesive streams and/or particulate material, or by reducing the force of the jets of air to manipulate the adhesive streams and/or particulate material to a lesser extent. In this manner, the use of the air blowers 511 may allow for shaping of the adhesive and/or particulate material, particularly influencing the extent to which the adhesive and/or particulate material is deposited at the forming surface 524 in the cross-machine direction 556. The air blowers 511 may help to comingle the particulate material and the adhesive as they are delivered from the particulate material delivery conduit 562 and the adhesive application nozzles 510, respectively, as the particulate material and the adhesive fall toward the forming surface 524. The air blowers 511 may have an opening diameter of about 0.5-5 mm, suitably about 1-3 mm, depending on the size of absorbent core being formed, line speed, number of air nozzles, air pressure, adhesive basis weight, and other process variables.

FIG. 15B depicts another exemplary absorbent material delivery chamber 560' disposed over forming drum 526'. The forming surface 524' is depicted disposed on the forming drum 526' extending between the drum rims 552'. In general, the embodiment shown in FIG. 15B may be similar to the embodiment shown in FIG. 15A. However, in the embodiment of FIG. 15B, the orientation of the particulate material delivery conduit 562' and the adhesive application nozzles 510' may be skewed with respect to the machine direction 554'. For example the particulate material delivery conduit 562' and the adhesive application nozzles 510' may be oriented at an angle 520 with respect to the machine direction 556'. The angle 520 may range from between one degree to ninety degrees.

In general, the angle 520 may be chosen in order to influence a cross-machine direction 554' spread of the deposited particulate material from the particulate material delivery conduit 562' and the adhesive from the adhesive application nozzles 510'. As can be seen in FIG. 15B, with the particulate material delivery conduit 562' and the adhesive application nozzles 510' oriented at the angle 520, the cross-machine direction 556' spread of the deposited particulate material and the adhesive may be greater than the cross-machine direction 556 spread of the deposited particulate material and the adhesive in FIG. 15A because the particulate material delivery conduit 562' and the adhesive application nozzles 510' span an initially greater cross-machine direction 556' distance than the distance the particulate material delivery conduit 562 and the adhesive application nozzles 510 span in the cross-machine direction 556.

In general, the components described above with respect to FIGS. 15A and 15B may be incorporated into any of the processes described with respect to apparatuses 20, 200, or 300. The components may be used in place of either of the first particulate material delivery chamber in any of the described processes or any subsequent particulate material delivery chamber. In this manner, the matrix of particulate material and adhesive formed by use of the components of FIG. 15A or 15B may be either formed on a base carrier sheet or on any prior application of particulate material or adhesive. In at least some embodiments, the disclosed apparatuses may comprise two or more instances of the components of FIGS. 15A and/or 15B to form absorbent cores that have two or more matrices, or a thicker region, of particulate material and adhesive disposed within an absorbent core.

The spread of the deposited matrix of particulate material and adhesive in the cross-machine direction 556 within formed absorbent cores may generally be less than the spread of other non-matrix applications of particulate material and adhesive of the absorbent cores. For instance, where the matrix of particulate material and adhesive is a deposited as a second application, the first application of particulate material (again, which may not be part of a matrix with adhesive) may span a majority of a cross-machine direction 556 width of the formed absorbent core. The matrix of particulate material and adhesive, however, may span in the cross-machine direction 556 less than the first application of particulate material. This may allow targeting of particulate material to areas of the absorbent core that will be most beneficial for absorption, e.g. where the particulate material in the matrix of particulate material and adhesive is only present in particular regions of the absorbent core. This may further allow for the overall particulate material content of the formed absorbent core to be less than if the matrix of particulate material and adhesive spanned the whole cross-machine direction 556 width of the absorbent core, or at least to the same extent as the first application of particulate material.

Figure 16:
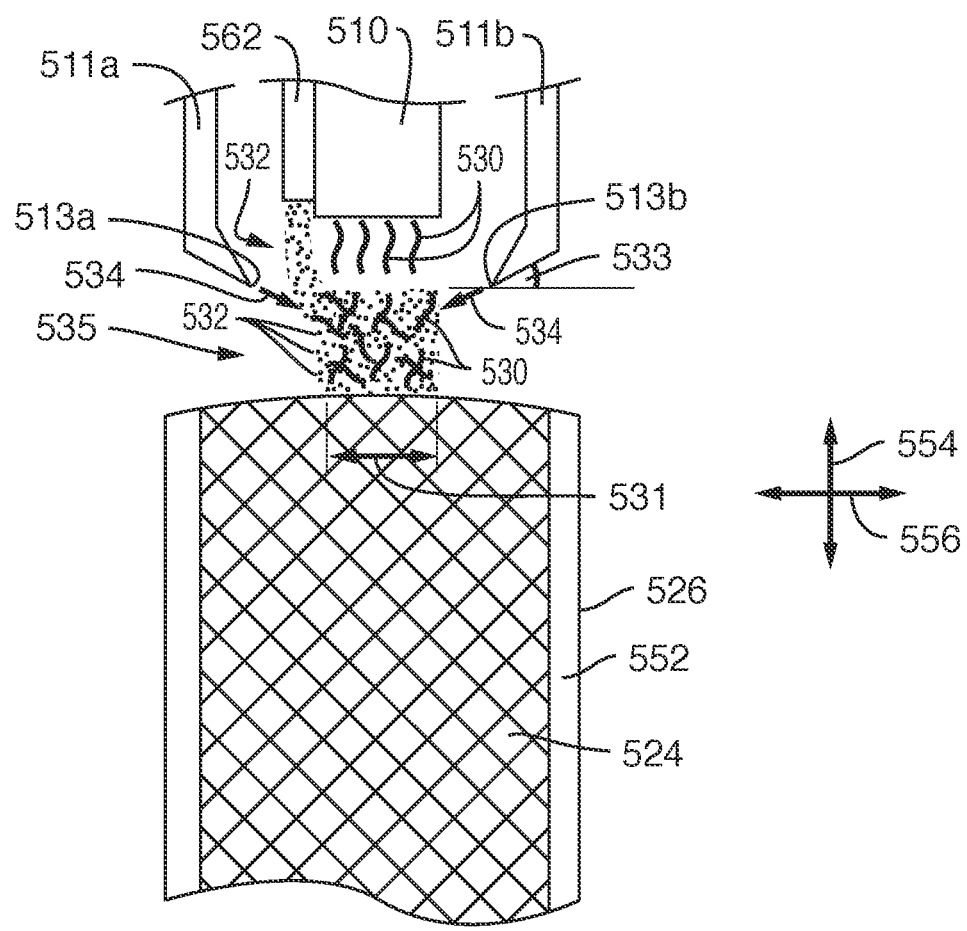
FIG. 16 is a side-view of the exemplary components of FIG. 15A.

FIG. 16 depicts a side view of the components described in FIGS. 15A and 15B. As can be seen in FIG. 16, adhesive 530 may exit adhesive application nozzles 510 and particulate material 532 may exit the particulate material delivery conduit 562 above air streams 534 created by air blowers 511a, 511b. As the particulate material 532 and the adhesive 530 travel toward the forming surface 524, the particulate material 534 and the adhesive 530 become entrained in air streams 534 and become comingled in region 535 above the forming surface 524. This can be seen in FIG. 16 as the adhesive 530 is intermixed with the particulate material 532 in the region 535 before being deposited at the forming surface 524 as a matrix of particulate material 532 and adhesive 530. Generally, the matrix of particulate material 532 and adhesive 530 deposited at the forming surface 524 may span in the cross-machine direction 556 a width 531. Again, it should be understood that air blowers 511a, 511b are option components. In embodiments where air blowers 511a, 511b are not present, the particulate material 532 and adhesive 530 may still intermix as they fall toward the forming surface 524. For instance, vacuum pressure may draw the particulate material 532 and adhesive 530 toward the forming surface 524 and cause the particulate material 532 and adhesive 530 to intermix.

In some embodiments, the rate of revolution of the forming drum 526 in the machine direction 554, the weight and volume of the particulate material 532 exiting the particulate material delivery conduit 562, the weight and volume of the adhesive 530 exiting the adhesive application nozzles 510, the strength of the air streams 534 from the air blowers 511a, 511b, and other process factors may be modified to create a width 531 that may be between about 5 cm and about 15 cm. In some embodiments, the strength of the vacuum within the forming drum 526 may also influence the width 531. For example, a stronger vacuum within the forming drum 526 may influence the particulate material 532 and the adhesive 530 as they fall toward the forming surface 524 and cause the particulate material 532 and the adhesive 530 to spread more in the cross-machine direction 556 than in comparison to a weaker vacuum within the forming drum 526.

Air blowers 511a, 511b may additionally include nozzles 513a, 513b that direct the streams of air 534 toward the particulate material 532 and the adhesive 530. In at least some embodiments, the nozzles 513a, 513b may be angled toward the forming surface 524 at an angle 533. The angle 533 may range between about zero degrees to about sixty degrees.

Figure 17:
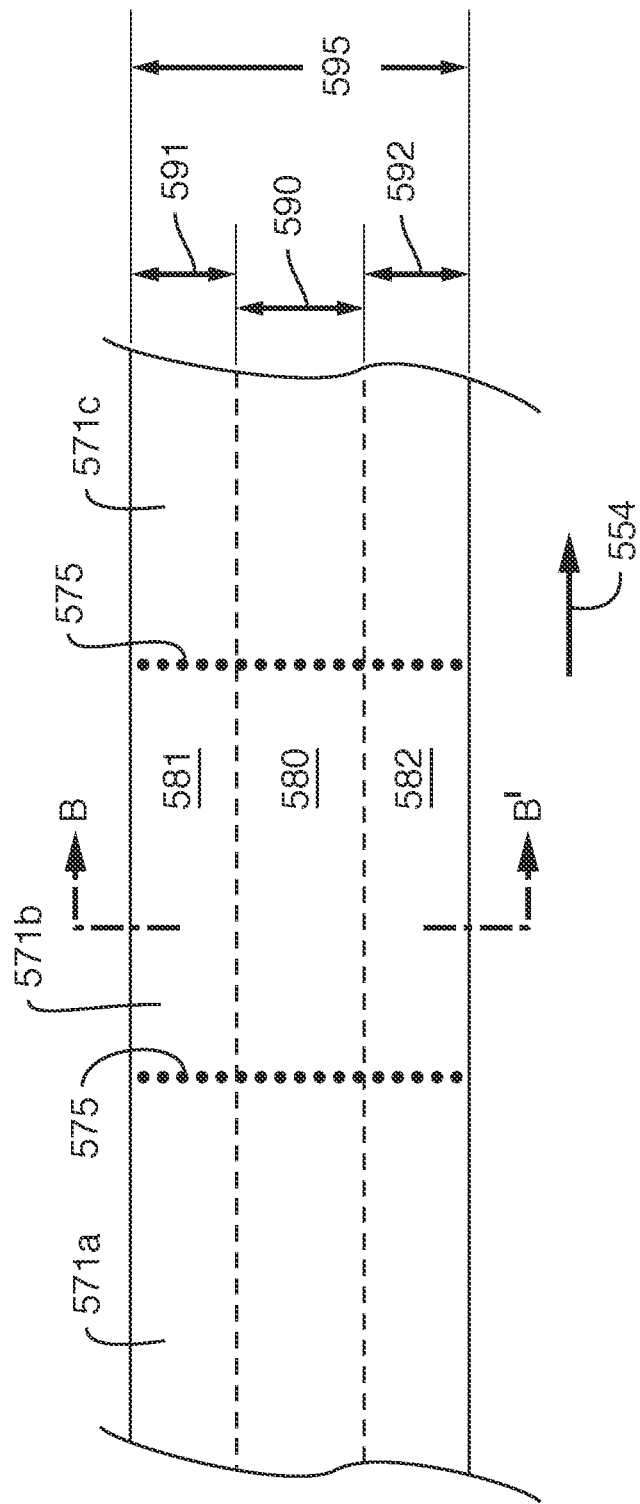
FIG. 17 is an illustration of a length of formed absorbent cores that may be formed using the components of FIG. 15A.

FIG. 17 depicts a length of formed absorbent cores 570 comprising connected, individual absorbent cores 571a-c that may be formed using any of the processes described herein and further including a matrix of particulate material and adhesive formed by the processes described with respect to FIGS. 15A, 15B, and 16. The connected, individual absorbent cores 571a-c may later be separated forming discrete individual absorbent cores, for example by cutting along cut lines 575.

The formed absorbent cores 571a-c may have an overall core width 595 and may include a center region 580 having a center width 590. The absorbent cores 571a-c may further include a first edge region 581 having a first edge region width 591 and a second edge region 582 having a second edge region width 592. In some embodiments, the center width 590 may generally correspond to the cross-machine direction 556 spread of the matrix region of particulate material and adhesive of the absorbent cores 571a-c. In these embodiments, the center width 590 may range between about one-quarter to about three-quarters of the overall core width 595. Accordingly, the cross-machine direction 556 spread of the matrix of particulate material and adhesive of the absorbent cores 571a-c may range between about one-quarter to about three-quarters of the overall core width 595. More generally, the center region 580 may correspond to a crotch region of the absorbent core 571a-c. For instance, in some embodiments, the absorbent cores 571a-c may be shaped, for instance as described with respect to FIGS. 10 and 11. In these embodiments, the center width 590 of the center region 580 may correspond to the width of the crotch region of these shaped absorbent cores. This may help to ensure that additional particulate material is located at positions of the absorbent cores where the additional particulate material is able to be most effective, while also ensuring that additional particulate material is not added to locations where the particulate material is not needed or would be less effective, thus helping to keep manufacturing costs down.

In these embodiments, then, the first edge region width 591 and the second edge region width 592 may range between about three-eighths and about one-eighth of the overall core width 595. In some specific examples, the overall core width 595 may be between about 3 cm and about 25 cm. In these examples, the center width 590 may range between about 0.75 cm and about 18.75 cm, or more generally between about 1 cm and about 20 cm. The first edge region width 591 and the second edge region width 592, then, may range generally between about 1 cm and about 10 cm.

Another feature of the absorbent cores 571a-c is that since the matrix of particulate material and adhesive spans only a portion of the overall core width 595, the different regions of the absorbent cores 571a-c may have different amounts of particulate material. For instance, in some embodiments, at least 25% of the total amount of particulate absorbent material in one of the absorbent cores 571a-c may be located within the center region 580. In other embodiments, at least 50% of the total amount of particulate material in one of the absorbent cores 571a-c may be located within the center region 580. In still further embodiments, at least 75% of the total amount of particulate material in one of the absorbent cores 571a-c may be located within the center region 580. These values may translate into particulate material and adhesive basis weights of between about 100 gsm and about 1000 gsm. Accordingly, the basis weights of the particulate material and adhesive located within the first edge region width 591 and the second edge region width 592 may range between about 50 gsm and about 400 gsm. These values may span a useful range for different absorbent articles where the cores 571a-c may be ultimately used.

Figure 18:
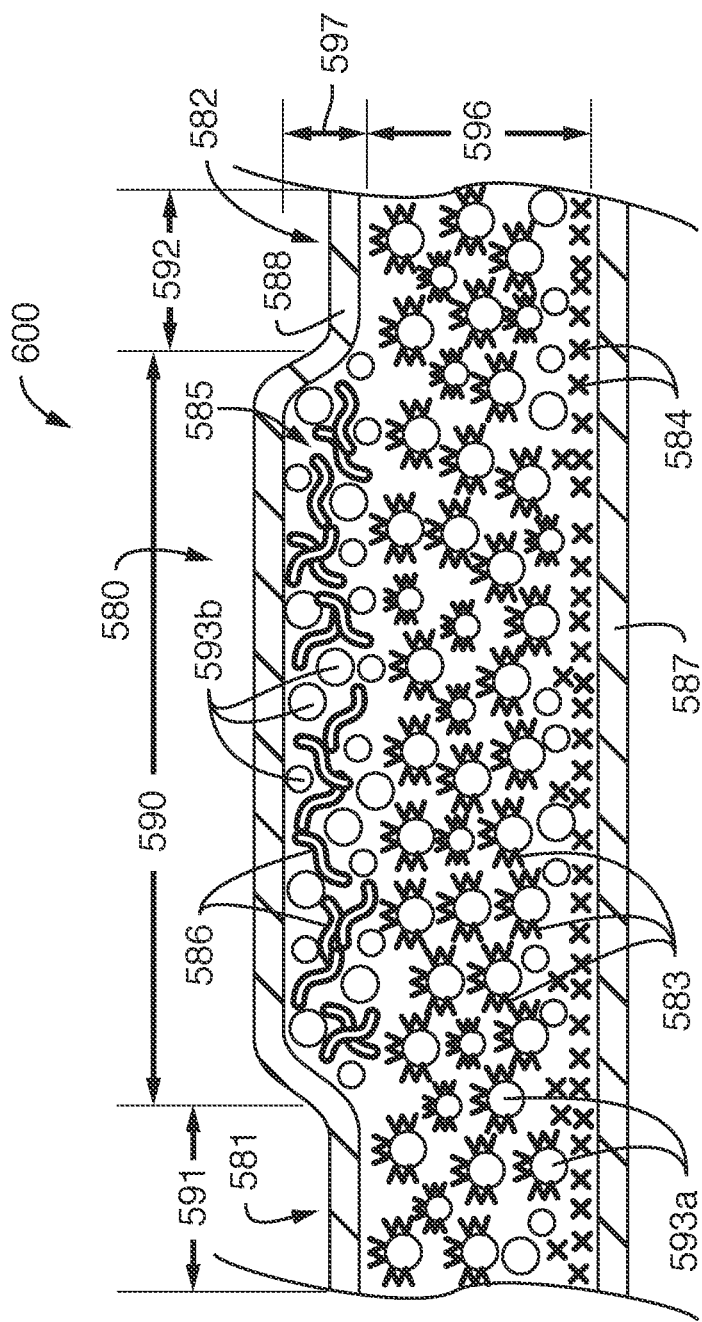
FIG. 18 depicts a cross-section of an exemplary absorbent core taken along line B-B' in FIG. 17 which includes a matrix layer.

FIGS. 18 and 19 depict cross-sections of exemplary absorbent cores 600 and 601 that may represent a cross-section of the absorbent core 571b taken along line B-B' in FIG. 17. In the example of FIG. 18, the absorbent core 600 may comprise a base carrier sheet 587. In at least some embodiments, a first adhesive 584, represented by the 'x's, may be disposed directly on the base carrier sheet 587. Absorbent core 600 further includes a first amount of particulate material 593a applied directly to the first adhesive 584 (or directly to the base carrier sheet 587 in embodiments that do not include the first adhesive 584 disposed directly on the base carrier sheet 587) forming region 596.

Although not necessary in all embodiments, absorbent core 600 may further include a second adhesive 583, as represented by the 'w's. In these embodiments, the second adhesive 583 may be applied onto the first amount of particulate material 593a that formed region 596. In at least some embodiments, the second adhesive 583 may comprise a spray application aqueous binder (SAAB) adhesive. In these examples, as shown in FIG. 18, the second adhesive 583 may penetrate into the particulate material 593a within region 596. Again, it should be understood that the second adhesive 583 may be applied only in some contemplated embodiments.

Whether a second adhesive 583 is present or not, a matrix of particulate material and adhesive 585 may be disposed adjacent to the first amount particulate material 593a that forms regions 596. The matrix of particulate material and adhesive 585 may generally comprise a second amount of particulate material 593b and adhesive fibers 586. The adhesive fibers 586 may be formed, for example, by adhesive application nozzles 510 described above with respect to FIGS. 15A, 15B, and 16. The matrix of particulate material and adhesive 585 may be generally disposed within region 597.

The matrix of particulate material and adhesive 585 forming region 596 may comprise particulate material and adhesive having a basis weight ranging between about 100 gsm to about 500 gsm. Additionally as can be seen, the matrix of particulate material and adhesive 585 may generally span throughout the center region 580, whereas the first amount of particulate material 593a may span throughout the whole width of the absorbent core 600, including throughout the first edge region 581 and the second edge region 582. Due to this fact, the center region 580 may generally have a higher basis weight, of both particulate material and adhesive, than either of the first edge region 581 and the second edge region 582.

Although not shown explicitly in FIG. 18, in at least some embodiments, the absorbent core 600 may additionally include a third adhesive disposed between the top carrier sheet 588 and matrix of particulate material and adhesive 585. The third adhesive may either may applied directly to the matrix of particulate material and adhesive 585 or may be applied directly to the top carrier sheet 588, in accordance with previously disclosed techniques.

Finally, a top carrier sheet 588 may be applied to the matrix of particulate material and adhesive 585 resulting in the top carrier sheet 588 being disposed directly on the matrix of particulate material and adhesive 585 or on the third adhesive. Additionally, as described previously, in some embodiments, the top carrier sheet 588 may be the bottom carrier sheet 587 folded onto the matrix of particulate material and adhesive 585 or the third adhesive to form the top carrier sheet 588.

FIG. 19 depicts exemplary absorbent core 601. Exemplary absorbent core 601 may comprise a base carrier sheet 587'. In at least some embodiments, a matrix of particulate material and adhesive 585' may then be disposed directly on the base carrier sheet 587'. Alternatively in other embodiments, a first adhesive 584' may be disposed directly on the base carrier sheet 587' and the matrix layer 585' may then be disposed directly on the first adhesive layer 584'. In either case, as can be seen in FIG. 19, the matrix of particulate material and adhesive 585' may only span across a portion of the absorbent core 601. For instance, the matrix of particulate material and adhesive 585' may only span across the center portion 580 of the absorbent core 601. The matrix of particulate material and adhesive 585' may comprise both particulate material 593b' and adhesive fibers 586'. As can be seen, particulate material 593b' and the adhesive fibers 586' are intermixed to form the matrix of particulate material and adhesive 585'. Additionally, the matrix of particulate material and adhesive 585' may comprise particulate material and adhesive having a basis weight between about 100 gsm to about 500 gsm.

The absorbent core 601 may further comprise other particulate material, e.g. particulate material 593a', that is not part of a matrix of particulate material and adhesive fibers. The other particulate material 593a' may have been applied to the absorbent core 601 after the matrix of particulate material and adhesive 585' had been applied to the absorbent core. The other particulate material 593a' may further be applied to the absorbent core 601 throughout the entire width of the absorbent core 601. Accordingly, as can be seen in FIG. 19, the other particulate material 593a' may span throughout all of regions 580-582, whereas the matrix of particulate material and adhesive 585' may only span throughout the center region 580. This may then result in the center portion 580 of the absorbent core 601 having a higher basis weight, both in terms of particulate material 592a' and 593b' and adhesive, than either of the first edge region 581 and the second edge region 582.

In some embodiments, a second adhesive 583' may be disposed on the other particulate material 593a'. For instance, the second adhesive 583' may be applied directly to the other particulate material 593a'. As shown in FIG. 19, the second adhesive 583' may be a spray application aqueous binder (SAAB) adhesive, and the second adhesive 583' may penetrate throughout the other particulate material 593a'. Although not shown in FIG. 19, in some instances, the second adhesive 583' may further penetrate the matrix of particulate material and adhesive 585'. However, in other embodiments, the second adhesive 583' may not be a SAAB adhesive. For example, the second adhesive 583' may be a hot-melt or other suitable adhesive. In these instances, the second adhesive 583' may be applied directly to the other particulate material 593a' and may not appreciably penetrate the other particulate material 593a', or the second adhesive 583' may be applied to the top carrier sheet 588' before the top carrier sheet 588' is applied to the other particulate material 593a'. In still further embodiments, the second adhesive 583' may be a SAAB adhesive, and the absorbent core 601 may additionally comprise a third adhesive that is a hot-melt adhesive disposed between the other particulate material 593a' and the top carrier sheet 588'. Accordingly, whether applied directly to the other particulate material 593a' or the top carrier sheet 588', the second adhesive 583' may be disposed generally between the other particulate material 593a' and the top carrier sheet 588'.

Finally, a top carrier sheet 588' is shown disposed adjacent to the other particulate material 593a'. Again, depending on the specific embodiment, the top carrier sheet 588' may be disposed directly on the other particulate material 593a' or there may be an adhesive disposed between the other particulate material 593a' and the top carrier sheet 588'. Additionally, as described previously, in some embodiments, the top carrier sheet 588' may be the bottom carrier sheet 587' folded onto the first particulate absorbent material layer 593' or the third adhesive layer 586' to form the top carrier sheet 588'.

The pulpless absorbent cores the present disclosure may be used in many different absorbent articles. For example, pulpless absorbent cores the present disclosure may be used in diapers and/or training pants in order to help absorb urine and other liquid discharge from babies and toddlers. The pulpless absorbent cores the present disclosure may additionally, or alternatively, be used in incontinence products, disposable underwear, and/or medical garments to help absorb liquid discharge from people who may not be able to control their ability to urinate or defecate. Even further, the pulpless absorbent cores the present disclosure may additionally, or alternatively, be used in feminine care articles to help absorb vaginal discharges. These are just some example absorbent articles in which the pulpless absorbent cores the present disclosure may be used. In general, the pulpless absorbent cores the present disclosure may be used in any suitable absorbent article application.

As various changes could be made in the above without departing from the scope of the invention, it is intended that all matter contained in the above description and shown in the accompanying drawings shall be interpreted as illustrative and not in a limiting sense.

I claim:

1. A method of forming an absorbent core, the method comprising:

moving a foraminous forming surface in a machine direction;

creating a pressure differential across the foraminous forming surface;

advancing a base carrier sheet on the foraminous forming surface in the machine direction;

applying a first adhesive and a first quantity of superabsorbent material onto the base carrier sheet; and depositing a matrix of adhesive and superabsorbent material directly onto the first adhesive and the first quantity of superabsorbent material, the matrix of adhesive and superabsorbent material comprising a second quantity of superabsorbent material and a second adhesive, the second quantity of superabsorbent material being dispensed from a superabsorbent material delivery conduit and the second adhesive comprising a fibrous adhesive dispensed from one or more application nozzles, the application nozzles located adjacent to the superabsorbent material delivery conduit at least partially in the machine direction and wherein the fibrous second adhesive and the second quantity of superabsorbent material mix prior to deposition onto the first adhesive and the first quantity of superabsorbent material.

2. The method of claim 1, wherein applying the first adhesive and the first quantity of superabsorbent material onto the base carrier sheet comprising depositing a matrix of the first adhesive and the first quantity of superabsorbent material onto the base carrier sheet, the first quantity of superabsorbent material being dispensed from a superabsorbent material delivery conduit and the first adhesive comprising a fibrous adhesive dispensed from one or more application nozzles, the application nozzles located adjacent to the superabsorbent material delivery conduit at least partially in a machine direction and wherein the fibrous first adhesive and the first quantity of superabsorbent material mix prior to deposition onto the base carrier sheet.

3. The method of claim 1, further comprising adhesive to the base carrier sheet prior to applying the first adhesive and the first quantity of superabsorbent material.

4. The method of claim 1, wherein the superabsorbent material delivery conduit and the one or more application nozzles dispensing the second adhesive are disposed within a superabsorbent material delivery chamber.

5. The method of claim 2, wherein the superabsorbent material delivery conduit and the one or more application nozzles dispensing the first adhesive are disposed within a superabsorbent material delivery chamber.

6. The method of claim 1, wherein the first quantity of superabsorbent material is applied onto the base carrier sheet to have a first cross-machine direction maximum width, the second quantity of superabsorbent material is applied to the first adhesive and the first quantity of superabsorbent material to have a second cross-machine direction maximum width, and wherein the second cross-machine direction maximum width is different than the first cross-machine direction maximum width.

7. The method of claim 6, wherein the first quantity of superabsorbent material is applied onto the base carrier sheet to have a plurality of cross-machine direction widths, and wherein the second cross-machine direction maximum width is less than or equal to a minimum cross-machine direction width of the applied first quantity of superabsorbent material.

8. The method of claim 6, wherein the second quantity of superabsorbent material is applied to the first adhesive and the first quantity of superabsorbent material to have a plurality of cross-machine direction widths.

9. The method of claim 1, wherein the superabsorbent material is gravity fed through the superabsorbent material delivery conduit.

10. A method of forming an absorbent core, the method comprising:
moving a foraminous forming surface in a machine direction;
creating a pressure differential across the foraminous forming surface;
advancing a base carrier sheet on the foraminous forming surface in the machine direction;
depositing a matrix of a first adhesive and a first quantity of superabsorbent material onto the base carrier sheet, the first quantity of superabsorbent material being dispensed from a first superabsorbent material delivery conduit and the first adhesive comprising a fibrous adhesive dispensed from one or more first application nozzles with the fibrous first adhesive and the first quantity of superabsorbent material mixing prior to deposition onto the base carrier sheet, the first application nozzles located adjacent to the first superabsorbent material delivery conduit at least partially in the machine direction; and
depositing a matrix of a second adhesive and a second quantity of superabsorbent material directly onto the matrix of the first adhesive and the first quantity of superabsorbent material, the second quantity of superabsorbent material being dispensed from a second superabsorbent material delivery conduit and the second adhesive comprising a fibrous adhesive dispensed from one or more second application nozzles with the fibrous second adhesive and the second quantity of superabsorbent material mixing prior to deposition onto the first adhesive and the first quantity of superabsorbent material, the second application nozzles located adjacent to the second superabsorbent material delivery conduit at least partially in a machine direction; and
directing air from one or more air blowers in a direction toward the first superabsorbent material delivery conduit.

11. The method of claim 10, further comprising directing air from one or more air blowers in a direction toward the second superabsorbent material delivery conduit.

12. The method of claim 10, wherein the one or more air blowers are disposed adjacent, in a cross-machine direction, to the one or more first application nozzles dispensing the fibrous first adhesive.

13. The method of claim 11, wherein the one or more air blowers directing air toward the second superabsorbent material delivery conduit are disposed adjacent, in a cross-machine direction, to the one or more second application nozzles dispensing the fibrous second adhesive.

14. The method of claim 10, wherein the one or more air blowers direct air toward the first superabsorbent material delivery conduit in opposite directions.

15. The method of claim 10, wherein the one or more air blowers directing air toward the second superabsorbent material delivery conduit are direct air toward the second superabsorbent material delivery conduit in opposite directions.

16. The method of claim 10, wherein the one or more air blowers directing air in a direction toward the first superabsorbent material delivery conduit are disposed between 10 mm and 100 mm from the first superabsorbent material delivery conduit.

17. The method of claim 11, wherein the one or more air blowers directing air in a direction toward the second superabsorbent material delivery conduit are disposed between 10 mm and 100 mm from the second superabsorbent material delivery conduit.

18. The method of claim 10, wherein the first superabsorbent material delivery conduit and the one or more first application nozzles dispensing the second adhesive are disposed within a superabsorbent material delivery chamber.

19. The method of claim 10, wherein the first quantity of superabsorbent material is applied onto the base carrier sheet to have a first cross-machine direction maximum width, the second quantity of superabsorbent material is applied to the first quantity of superabsorbent material to have a second cross-machine direction maximum width, and wherein the second cross-machine direction maximum width is different than the first cross-machine direction maximum width.

20. The method of claim 19, wherein the first quantity of superabsorbent material is applied onto the base carrier sheet to have a plurality of cross-machine direction widths, and wherein the second cross-machine direction maximum width is less than or equal to a minimum cross-machine direction width of the applied first quantity of superabsorbent material.

* * * * *